United States Patent [19]

Dubs et al.

[11] Patent Number: 5,510,402
[45] Date of Patent: Apr. 23, 1996

[54] CARBOXYLIC ACID ESTERS OF HYDROXYPHENYLALKANOLS AS STABILIZERS

[75] Inventors: Paul Dubs, Marly; Rita Pitteloud, Praroman, both of Switzerland

[73] Assignee: Ciba-Geigy Corporation, Tarrytown, N.Y.

[21] Appl. No.: 158,177

[22] Filed: Nov. 24, 1993

Related U.S. Application Data

[63] Continuation of Ser. No. 46,044, Apr. 12, 1993, abandoned, which is a continuation-in-part of Ser. No. 18,602, Feb. 17, 1993, abandoned.

[30] Foreign Application Priority Data

Feb. 24, 1993 [CH] Switzerland ................. 547/92

[51] Int. Cl.⁶ ............... C07C 323/51; C07C 69/708; C07C 69/34; C08K 5/3; C08K 5/134; C08K 5/15; C08K 5/11; C08K 5/36
[52] U.S. Cl. ............... 524/84; 524/110; 524/239; 524/240; 524/289; 524/291; 524/334; 549/79; 549/485; 560/127; 560/152; 560/154; 560/171; 560/173; 560/193; 560/221; 568/763; 568/766
[58] Field of Search ................. 568/763, 766; 560/127, 152, 154, 171, 173, 193, 221; 524/289, 291, 84, 110, 239, 240, 334; 549/79, 485

[56] References Cited

U.S. PATENT DOCUMENTS

| | | | |
|---|---|---|---|
| 3,763,287 | 10/1973 | Chiddix et al. | 568/763 |
| 3,919,097 | 11/1975 | Park | 252/48.6 |
| 4,104,252 | 8/1978 | Hechenbleikner et al. | 560/171 |
| 4,132,702 | 1/1979 | Schmidt et al. | 524/291 |
| 4,260,832 | 4/1981 | Parker et al. | |
| 4,261,912 | 4/1981 | Tracy | 560/193 |
| 4,311,637 | 1/1982 | Cottman | 560/17 |
| 4,333,868 | 6/1982 | Schmidt et al. | 524/152 |
| 4,633,008 | 12/1986 | Oonishi et al. | 560/193 |
| 4,910,286 | 3/1990 | White et al. | 528/272 |

FOREIGN PATENT DOCUMENTS

| | | |
|---|---|---|
| 0292672 | 11/1988 | European Pat. Off. |
| 0171139 | 7/1989 | European Pat. Off. |
| 0349380 | 1/1990 | European Pat. Off. |
| 2147544 | 7/1972 | Germany |
| 7905000 | 6/1979 | Netherlands |
| 1509876 | 5/1978 | United Kingdom |
| WO88/08424 | 11/1988 | WIPO |

OTHER PUBLICATIONS

CA 84: 32016K (1976).
CA 76: 153360M (1972).
CA 113:58701X (1990).
CA 93:240542S (1980).
CA 84:106614C (1990).
CA 106:156001u (1990).
Tetrahedron 36:2409–33 (1980).
C.A. 106(19):156001u (1987).
C.A. 99(15) 121916F (1983).
C.A. 81(16):92669y (1974).
Chem. Abst. Service Registry Handbook No. 107608–34–4 (1987) Supplement).
Chem. Abst. 111–79247C (1989).
Richard Levy Rev. Gen. Caout. Plast., 51(4), 243(1974).

Primary Examiner—Veronica P. Hoke
Attorney, Agent, or Firm—Michele A. Kovaleski; Luther A. R. Hall

[57] ABSTRACT

The novel compounds of the formula I

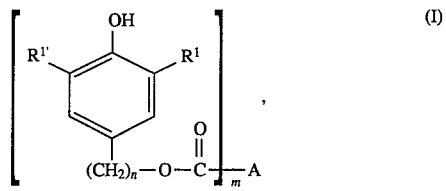

in which n is an integer from the range from 4 to 8 and m is an integer from the range from 1 to 4, A is the aliphatic, aromatic, araliphatic or heterocyclic radical of a monobasic to tetrabasic carboxylic acid, and $R^1$ and $R^{1'}$, independently of one another, are $C_1$–$C_{24}$alkyl or $C_5$–$C_8$cycloalkyl, are suitable for stabilizing organic material against thermal, oxidative or actinic degradation.

18 Claims, No Drawings

CARBOXYLIC ACID ESTERS OF HYDROXYPHENYLALKANOLS AS STABILIZERS

This is a continuation of application Ser. No. 08/046,044, filed on Apr. 12, 1993, now abandoned, which is a continuation-in-part of application Ser. No. 08/018,602, filed on Feb. 17, 1993, now abandoned.

The present invention relates to novel carboxylic acid esters of ω-(3,5-dialkyl-4-hydroxyphenyl)alkanols, the organic materials stabilised against thermal, oxidative and actinic degradation using these compounds, the use of the novel compounds as stabilisers and novel ω-(3,5-dialkyl-4-hydroxyphenyl)alkanols.

The use of the esters of ω-hydroxyphenyl)-α-carboxylic acid esters as stabilisers for organic materials is known.

A number of publications relate to corresponding inverse esters: Chem. Abstr. 84 32016k, DE-A-2 147 544, EP-B-171 139, EP-A-349 380, NL-A-79-05000, GB-A-1 509 876, Chem. Abstr. 84 106614c, Chem. Abstr. 106 156001u, U.S. Pat. Nos. 4,910,286, 4,311,637, 4,104,252 and 3,919,697 describe carboxylic acid esters of 3-(3,5-di-tert-butyl-4-hydroxyphenyl)alkan-1-ols, 3-(3-tert-butyl-5-methyl-4-hydroxyphenyl)alkan-1-ols and individual 4-(3,5-dialkyl-4-hydroxyphenyl)alkan-1-ols, as well as their use as polymer stabilisers.

Several novel carboxylic acid esters of ω-(3,5-dialkyl-4-hydroxyphenyl)alkanols have now been found which have particularly good stabiliser properties.

One subject of the present invention therefore comprises compounds of the formula I

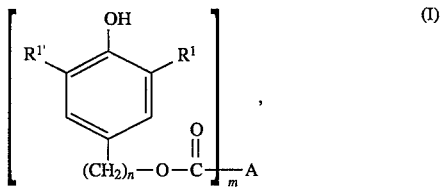

in which n is an integer from the range from 4 to 8 and m is an integer from the range from 1 to 4;

if m=1, A is $C_1$–$C_{25}$alkyl, which is unsubstituted or substituted by $C_5$–$C_8$cycloalkyl; or is $C_2$–$C_{25}$alkyl which is interrupted by $C_5$–$C_8$cycloalkyl or one or more of the groups —S—, —O— and/or —NR$^2$—; or, if m=1, A is $C_5$–$C_8$cycloalkyl, which is unsubstituted or substituted by $C_1$–$C_{12}$alkyl or $C_2$–$C_{12}$alkenyl; $C_6$–$C_8$cycloalkenyl, which is unsubstituted or substituted by $C_1$–$C_{12}$alkyl or $C_2$–$C_{12}$alkenyl; phenyl, which is unsubstituted or substituted by $C_1$–$C_{12}$alkyl or $C_2$–$C_{12}$alkenyl; naphthyl, which is unsubstituted or substituted by $C_1$–$C_{12}$alkyl or $C_2$–$C_{12}$alkenyl; biphenyl, which is unsubstituted or substituted by $C_1$–$C_{12}$alkyl or $C_2$–$C_{12}$alkenyl; or $C_2$–$C_{25}$alkenyl; $C_6$–$C_{10}$bicycloalkenyl; $C_7$–$C_{12}$phenylalkyl; $C_8$–$C_{12}$phenylalkenyl; $C_{11}$–$C_{16}$naphthylalkyl; $C_{12}$–$C_{16}$naphthylalkenyl; $C_{13}$–$C_{18}$biphenylalkyl; $C_{14}$–$C_{18}$biphenylalkenyl; or a group of the formula II

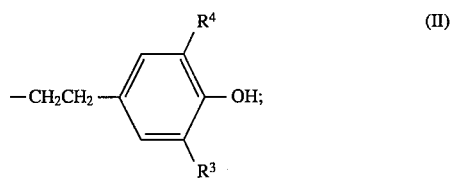

if m=2, A is a direct bond; $C_1$–$C_{12}$alkylene; $C_2$–$C_{12}$alkenylene; $C_5$–$C_8$cycloalkylene, which is unsubstituted or substituted by $C_1$–$C_{12}$alkyl or $C_2$–$C_{12}$alkenyl; $C_6$–$C_8$cycloalkenylene, which is unsubstituted or substituted by $C_1$–$C_{12}$alkyl or $C_2$–$C_{12}$alkenyl; $C_6$–$C_{10}$bicycloalkenylene; phenylene; naphthylene; a divalent heterocyclic radical from the group comprising furan, thiophene or pyrrole, which is saturated on the nitrogen atom by hydrogen or the substituent —R$^2$; or, if m=2, A is $C_2$–$C_{36}$alkylene which is interrupted by $C_5$–$C_8$cycloalkylene or phenylene or at least one of the groups —S—, —O— or —NR$^2$—;

if m=3, A is $C_1$–$C_8$alkanetriyl; $C_2$–$C_8$alkenetriyl; benzenetriyl; naphthalenetriyl; a trivalent group of the formula

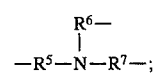

or $C_2$–$C_{18}$alkanetriyl, which is interrupted by at least one of the groups —S—, —O— or —NR$^2$—; or, if m=4, A is a benzene radical, naphthyl radical, tetrahydrofuryl radical or cyclohexyl radical having 4 free valencies;

R$^1$ and R$^{1'}$, independently of one another, are $C_1$–$C_{24}$alkyl or $C_5$–$C_8$cycloalkyl;

R$^2$ is H or $C_1$–$C_4$alkyl;

R$^3$ and R$^4$, independently of one another, are $C_1$–$C_4$alkyl; and

R$^5$, R$^6$ and R$^7$, independently of one another, are $C_1$–$C_3$alkylene.

$C_1$–$C_{24}$Alkyl or $C_5$–$C_8$cycloalkyl R$^1$ and R$^{1'}$ are for example, independently of one another, methyl, ethyl, propyl, butyl, pentyl, hexyl, heptyl, octyl, nonyl, decyl, cyclopentyl, cyclohexyl, cycloheptyl or cyclooctyl.

R$^{1'}$ is preferably secondary or tertiary $C_3$–$C_{24}$alkyl, for example 2-butyl (sec-butyl), tert-butyl, 2-pentyl, 2-hexyl or 3-hexyl, or R$^{1'}$ is $C_5$–$C_8$cycloalkyl, for example cyclohexyl, and R$^1$ is $C_1$–$C_{10}$alkyl or $C_5$–$C_8$cycloalkyl.

R$^{1'}$ is particularly preferentially secondary or tertiary $C_3$–$C_{18}$alkyl or $C_5$–$C_8$cycloalkyl, for example isopropyl, sec-butyl, tert-butyl or cyclohexyl, and R$^1$ is $C_3$–$C_8$alkyl or $C_5$–$C_8$cycloalkyl or is methyl.

Particularly preferred compounds of the formula I are those in which R$^1$ is methyl, tert-butyl or cyclohexyl, in particular methyl, and R$^{1'}$ is tert-butyl or cyclohexyl, in particular tert-butyl.

$C_1$–$C_4$Alkyl R$^2$, R$^3$ and R$^4$ are methyl, ethyl, 1-propyl (n-propyl), 2-propyl (isopropyl), 1-butyl (n-butyl), 2-butyl (sec-butyl), 2-methylpropyl (isobutyl) or 1,1-dimethylethyl (tert-butyl); methyl or tert-butyl is preferred.

$C_1$–$C_3$Alkylene R$^5$, R$^6$ and R$^7$ are methylene, 1,1- or 1,2-ethylene, or 1,1-, 1,2-, 2,2 or 1,3-propylene. Methylene is preferred.

If A is $C_1$–$C_{25}$alkyl, it is a branched or straight-chain radical, for example methyl, ethyl, propyl, isopropyl, n-butyl, sec-butyl, isobutyl, t-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, eicosyl, docosyl or pentacosyl; straight-chain alkyl is preferred and straight-chain $C_6$–$C_{18}$alkyl is particularly preferred.

As $C_1$–$C_{25}$alkyl substituted by $C_5$–$C_8$cycloalkyl, A is, for example, cyclopentylmethyl, cyclohexylmethyl, cycloheptylmethyl, cyclooctylmethyl, cyclohexylethyl, 2-cyclohexyl-n-propyl, 3-cyclohexyl-n-propyl or 4-cyclohexyl-n-butyl.

As $C_2$-$C_{25}$alkyl interrupted by $C_5$-$C_8$cycloalkyl or one or more of the groups —S—, —O— and/or —NR²—, A is one of the alkyl radicals described above, with the exception of methyl, in the chain of which cyclopentylene or cyclopentylidene, cyclohexylene or cyclohexylidene, cycloheptylene or cycloheptylidene, cyclooctylene or cyclooctylidene is inserted at one point or the abovementioned groups containing hetero atoms are inserted at one or more points. A therefore, for example, has the formulae

—CH₂—S—C₄H₉, —C₂H₄—O—C₂H₄—O—C₁₂H₂₅, —C₁₈H₃₆—N(C₄H₉)₂.

As $C_5$-$C_8$cycloalkyl or $C_6$-$C_8$cycloalkenyl which is unsubstituted or substituted by $C_1$-$C_{12}$alkyl or $C_2$-$C_{12}$alkenyl, A can be, for example: cyclopentyl, cyclohexyl, cycloheptyl, cyclooctyl, 2- or 4-methylcyclohexyl, dimethylcyclohexyl, trimethylcyclohexyl, t-butylcyclohexyl, 2-cyclohexenyl, 3-cycloheptenyl, cyclooctatetraenyl or 4-tert-butylcyclohex-2-enyl. Cyclohexyl and cyclohexenyl, especially cyclohexyl, are preferred.

As phenyl, naphthyl or biphenyl substituted by $C_1$-$C_{12}$alkyl or $C_2$-$C_{12}$alkenyl, A is, inter alia, methylphenyl, dimethylphenyl, trimethylphenyl, ethylphenyl, vinylphenyl, diethylphenyl, isopropylphenyl, tert-butylphenyl, di-tert-butylphenyl, methyl-di-t-butylphenyl, 1,1,3,3-tetramethylbutylphenyl and 1,1,3,3,5,5-hexamethylhexylphenyl, dodecenylphenyl, 1-methylnaphthyl, 2-methylnaphthyl, 1-ethylnaphthyl, 2-propylbiphenyl-4-yl or 4-(1-hex-3-enyl)biphenyl-8-yl. Phenyl, which is unsubstituted or substituted by 1–3, for example 1–2 and in particular 1 $C_1$-$C_4$alkyl group(s), in particular methyl, is preferred.

$C_2$-$C_{25}$Alkenyl A is, for example, vinyl, propenyl, isopropenyl, 2-butenyl, 3-butenyl, isobutenyl, n-penta-2,4-dienyl, 3-methylbut-2-enyl, n-oct-2-enyl, n-dodec-2-enyl, isododecenyl, n-octadec-2-enyl or n-octadec-4-enyl.

$C_7$-$C_{12}$Phenylalkyl, $C_7$-$C_{12}$phenylalkenyl, $C_{11}$-$C_{16}$naphthylalkyl, $C_{11}$-$C_{16}$naphthylalkenyl, $C_{13}$-$C_{18}$biphenylalkyl or $C_{13}$-$C_{18}$biphenylalkenyl A is $C_1$-$C_6$alkyl or $C_1$-$C_6$alkenyl substituted by phenyl, naphthyl or biphenyl, for example benzyl, phenethyl, 3-phenylpropyl, α-methylbenzyl, α,α-dimethylbenzyl, 2-phenylethenyl, 1-phenylprop-2-enyl, 6-phenylhexyl, 1-naphthylmethyl, 2-naphthylmethyl, 1-naphthyleth-1-yl, 2-(4-biphenylyl)prop-2-yl or 1-(4-biphenylyl)pent-3-en-1-yl.

$C_6$-$C_{10}$Bicycloalkenyl or $C_6$-$C_{10}$bicycloalkenylene A is an unsaturated bicyclic, monovalent or divalent radical of 6 to 10 carbon atoms which as a monovalent radical can be, for example, bicyclo[2.2.1]hepta-5-en-2-yl and as a divalent radical can have, for example, the formulae

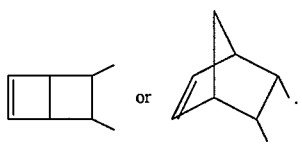

The divalent (for m=2), trivalent (for m=3) and tetravalent radicals A (for m=4) are derived from the monovalent radicals mentioned above. A divalent radical differs from the corresponding monovalent radical in that it contains an open bond in place of a hydrogen atom and a trivalent radical differs from the corresponding monovalent radical in that it contains two open bonds in place of two hydrogen atoms; a tetravalent radical differs from the corresponding monovalent radical in that it Contains three open bonds in place of three hydrogen atoms. Thus, within the framework of the indicated meanings, for example, A, as a divalent radical, can also be methylene, ethylene, —CH₂—C(CH₃)₂—CH₂—, prop-2-enylidene, 1,3-propylene, 1,4-butylene, 1,5-pentylene, 1,6-hexylene, o-, m- or p-phenylene,

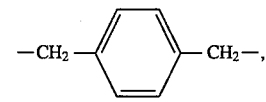

—C₂H₄—S—C₂H₄— or —C₂H₄—O—C₂H₄—, as a trivalent radical can be, for example,

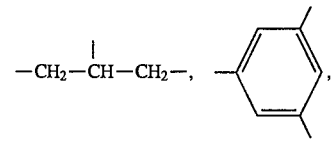

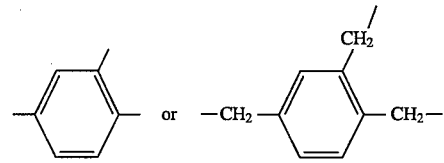

and as a trivalent radical can be, for example,

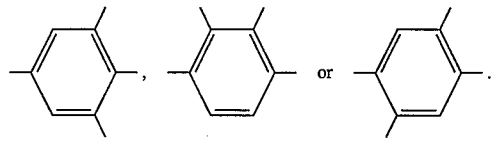

The novel esters of the formula I can be prepared by conventional esterification or transesterification methods from ω-hydroxyphenylalkanols of the formula IV

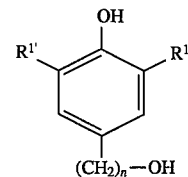

(IV) and organic carboxylic acids of the formula V

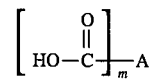

(V) or derivatives of such carboxylic acids, for example by methods such as are described in Tetrahedron 36, 2409 (1980). The symbols R¹, R¹', A, n and m in the formulae IV and V have the meanings indicated above for formula I. Suitable carboxylic acid derivatives are, for example, anhydrides, chlorides or lower alkyl esters, for example methyl or ethyl esters. Suitable esterification catalysts, such as mineral acids (for example sulfuric acid) or sulfonic acids (for example p-toluenesulfonic acid) can be used in the syntheses if appropriate.

The reaction can be carried out in a manner known per se, expediently by adding one of the two educts to the second educt and mixing the two reactants thoroughly, preferably with the exclusion of oxygen. The reaction can be carried out in the presence of a solvent, for example toluene, or also without a solvent. The temperature control is not critical; the temperature can be between the melting point and the boiling point of the reaction mixture, for example between −50° and 100° C., preferably between 0° and 50° C. The purification of the resulting product can also be carried out in accordance with known methods, for example by washing with water/HCl, extraction with an organic solvent, crystallisation and/or chromatography. Preferred solvents for the extraction and for the chromatographic purification step are hexane, ethyl acetate or mixtures thereof.

If the derivative of the carboxylic acid of the formula V used in the reaction is the acid chloride, an acid acceptor is expediently added to the reaction mixture. Suitable acid acceptors are, for example, amines, such as pyridine or triethylamine. Preferably the amount of the acid acceptor is at least equivalent to the amount of the acid chloride and is, for example, 1 to 2 equivalents, in particular 1.2 to 1.7 equivalents, with respect to the acid chloride.

If the reaction is carried out as a transesterification of an alcohol of the formula IV with the ester of a carboxylic acid of the formula V, conventional transesterification catalysts are expediently added to the reaction mixture. Such catalysts are, for example, organic or inorganic bases (for example lithium amide, lithium methoxide, potassium hydroxide and the like) or Lewis acids (for example dibutyltin oxide).

If the carboxylic acid of the formula V and the alcohol of the formula IV are used directly as educts, the reaction is expediently carried out using a water separator, distilling off water and/or using reagents which absorb liberated water, for example, dicyclohexylcarbodiimide.

The use of mixtures of carboxylic acids of the formula V or their derivatives can be of particular practical interest in the preparation of compounds of the formula I. Such mixtures can be used for the synthesis in the manner described above, corresponding mixtures of compounds of the formula I being obtained. Mixtures of compounds of the formula I can be used as such as stabilisers.

Alcohols of the formula IV are themselves also effective as stabilisers. Compositions containing (a) an organic material sensitive to oxidative, thermal and/or actinic degradation and (b) a compound of the formula IV, and also the use of compounds of the formula IV for stabilising organic material against oxidative, thermal or actinic degradation, are therefore further subjects of the invention.

The compositions according to the invention preferably contain those compounds of the formula IV in which $R^{1'}$ has the meaning of secondary or tertiary $C_3$–$C_{24}$alkyl or $C_5$–$C_8$cycloalkyl; and $R^1$ has the meaning $C_1$–$C_{10}$alkyl or $C_5$–$C_8$cycloalkyl. Particularly preferentially, $R^{1'}$ has the meaning of secondary or tertiary $C_3$–$C_{18}$alkyl or $C_5$–$C_8$cycloalkyl, for example isopropyl, sec-butyl, tert-butyl or cyclohexyl, and $R^1$ is $C_3$–$C_8$alkyl or $C_5$–$C_8$cycloalkyl or is methyl.

Compounds of the formula IV in which $R^1$ is methyl, tert-butyl or cyclohexyl, in particular methyl, and $R^{1'}$ is tert-butyl or cyclohexyl, in particular tert-butyl, are particularly preferred in the compositions according to the invention.

The compositions according to the invention preferably contain those compounds of the formula IV in which n is a number from the range 5 to 8, for example 6 to 8 and in particular the number 6.

The alcohols of the formula III described further below are also particularly preferred in the compositions according to the invention.

The ω-(hydroxyphenyl)alkanols of the formula IV can be prepared by known processes or analogously to such processes. Thus, the compounds of the formula IV are obtainable, for example, by the process described in U.S. Pat. No. 4,260,832 or by a process analogous to this. The corresponding 2,6-disubstituted phenols are then reacted with α,ω-alkandiols in the presence of alkali metal, alkali metal hydroxides or alkali metal alkoxides at temperatures of 200° to 300° C. with removal of the water formed during the reaction.

The product can then be isolated by conventional methods and used for reaction with carboxylic acid derivatives of the formula V; however, it is also possible to use the crude product directly without further purification for the preparation of compounds of the formula I.

If a 2,6-disubstituted phenol in which none or at most one of the alkyl or cycloalkyl substituents is tert-butyl is used in place of the starting phenols described in U.S. Pat. No. 4,260,832, novel compounds of the formula III

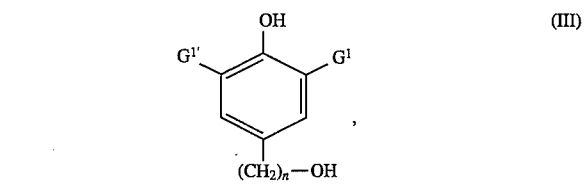

in which $G^1$ and $G^{1'}$ have the meanings indicated further above for $R^1$ and $R^{1'}$, but with the exception of tert-butyl for $G^1$, are obtained. As defined further above for formula I, n is an integer from the range 4 to 8.

A compound of the formula III is also a subject of the invention.

Preferred compounds of the formula III are those in which $G^{1'}$ has the meaning of secondary or tertiary $C_3$–$C_{24}$alkyl or $C_5$–$C_8$cycloalkyl; and $G^1$ has the meaning $C_1$–$C_{10}$alkyl or $C_5$–$C_8$cycloalkyl. $G^{1'}$ particularly preferentially has the meaning of secondary or tertiary $C_3$–$C_{18}$alkyl or $C_5$–$C_8$cycloalkyl, for example isopropyl, sec-butyl, tert-butyl or cyclohexyl, and $G^1$ is $C_3$–$C_8$alkyl with the exception of tert-butyl, or is $C_5$–$C_8$cycloalkyl or methyl.

Compounds of the formula III in which $G^1$ is methyl or cyclohexyl, in particular methyl, and $G^{1'}$ is tert-butyl or cyclohexyl, in particular tert-butyl, are preferred in particular.

Those compounds of the formula III in which n is a number from the range 5 to 8, for example 6 to 8 and in particular the number 6, are preferred.

Further processes by which, or analogously to which, compounds of the formula III and compounds of the formula IV can be prepared are described or referred to in, for example, DE-A-2 147 544 and in NL-A-79-05000.

As described above, the radical A in formula I is derived from a m-basic carboxylic acid. The acids can be aromatic, aliphatic, mixed aromatic-aliphatic, cycloaliphatic or bicycloaliphatic acids or unsaturated derivatives thereof, for example the following acids: caprylic acid, acetic acid, stearic acid, polyisobutenylsuccinic acid, n-hexacosanoic acid, trimethylacetic acid, propionic acid, isovaleric acid, lauric acid, oleic acid, acrylic acid, methacrylic acid, sorbic acid, linolenic acid, maleic acid, itaconic acid, glutaconic acid, dibasic acids, such as oxalic acid, succinic acid, iso-dodecylsuccinic acid, glutaric acid, adipic acid, pimelic acid, suberic acid, azelic acid or sebacic acid, the polymers of fatty acids, such as the dimers and trimers thereof of the type described, for example, in Ind. and Eng. Chem. 33, 86-89 (1941), hetero atom-containing acids, for example, nitrilotriacetic acid, cycloaliphatic acids, such as cyclohexanecarboxylic acid, 1,2- and 1,4-cyclohexanedicarboxylic acid and naphthenic acids, including, for example, cyclopentanecarboxylic acid, cyclopentylacetic acid, 3-methylcyclopentylacetic acid, camphor acid, 4-methylcyclohexanecarboxylic acid and 2,4,6-trimethylcyclohexanecarboxylic acid, bicyclo[2.2.2]octa-5-ene-2,3-dicarboxylic acid and bicyclo[2.2.1]hepta-5-ene-2-carboxylic acid, aromatic carboxylic acids, such as benzoic acid, o-, m- and p-toluic acid, phthalic acid, terephthalic acid, trimellitic acid, trimesic acid, 1,2,4,5benzenetetracarboxylic acid, diphenic acid, 1-naphthoic acid, 2-naphthoic acid, naphthalene-1,8-dicarboxylic acid, naphthalene-1,4-dicarboxylic acid, naphthalene-1,4,5-tricarboxylic acid and the like, paraffinic ω-aryl acids, such as phenylacetic acid, hydrocinnamic acid, phenylbutyric acid, γ-(1-naphthyl)butyric acid, δ-phenylene-n-valeric acid, ε-phenyl-n-caproic acid, o-, m- or p-phenylenediacetic acid or o-phenyleneacetic-βpropionic acid, and also unsaturated phenyl acids, for example, cinnamic acid.

Compounds of the formula Ia

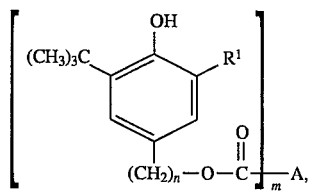

in which n is an integer from the range from 4 to 8 and m is an integer from the range from 1 to 3, if m=1, A is $C_1$–$C_{25}$alkyl, which is unsubstituted or substituted by $C_5$–$C_8$cycloalkyl, or is $C_2$–$C_{25}$alkyl, which is interrupted by $C_5$–$C_8$cycloalkyl or one or more of the groups —S—, —O— and/or —$NR^2$—, or, if m=1, A is $C_5$–$C_8$cycloalkyl, which is unsubstituted or substituted by $C_1$–$C_{12}$alkyl or $C_2$–$C_{12}$alkenyl, $C_6$–$C_8$cycloalkenyl, which is unsubstituted or substituted by $C_1$–$C_{12}$alkyl or $C_2$–$C_{12}$alkenyl, phenyl, which is unsubstituted or substituted by $C_1$–$C_{12}$alkyl or $C_2$–$C_{12}$alkenyl, naphthyl, which is unsubstituted or substituted by $C_1$–$C_{12}$alkyl or $C_2$–$C_{12}$alkenyl, biphenyl, which is unsubstituted or substituted by $C_1$–$C_{12}$alkyl or $C_2$–$C_{12}$alkenyl, or A is $C_2$–$C_{25}$alkenyl, $C_6$–$C_{10}$bicycloalkenyl, $C_7$–$C_{12}$phenylalkyl, $C_7$–$C_{12}$phenylalkenyl, $C_{11}$–$C_{16}$naphthylalkyl, $C_{11}$–$C_{16}$naphthylalkenyl, $C_{13}$–$C_{18}$biphenylalkyl, $C_{13}$–$C_{18}$biphenylalkenyl, or a group of the formula II

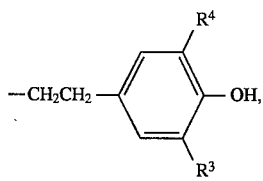

if m=2, A is a direct bond, $C_1$–$C_{12}$alkylene, $C_2$–$C_{12}$alkenylene, $C_5$–$C_8$cycloalkylene, which is unsubstituted or substituted by $C_1$–$C_{12}$alkyl or $C_2$–$C_{12}$alkenyl, or A is $C_6$–$C_8$cycloalkenylene, which is unsubstituted or substituted by $C_1$–$C_{12}$alkyl or $C_2$–$C_{12}$alkenyl, or A is $C_6$–$C_{10}$bicycloalkenylene, phenylene, naphthylene or $C_2$–$C_{18}$alkylene which is interrupted by $C_5$–$C_8$cycloalkylene or phenylene or at least one of the groups —S—, —O— or —$NR^2$—, if m=3, A is $C_1$–$C_8$alkanetriyl, $C_2$–$C_8$alkenetriyl, benzenetriyl, naphthalenetriyl, a trivalent group of the formula

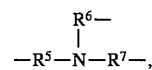

or $C_2$–$C_{18}$alkanetriyl which is interrupted by at least one of the groups —S—, —O— or —$NR^2$—, $R^1$ is methyl or tert-butyl, $R^2$ is H or $C_1$–$C_4$alkyl, $R^3$ and $R^4$, independently of one another, are $C_1$–$C_4$alkyl, and $R^5$, $R^6$ and $R^7$, independently of one another, are $C_1$–$C_3$alkylene, are a preferred subject of the invention.

Preferred compounds of the formula I are those in which n is an integer from the range from 4 to 8 and m is an integer from the range from 1 to 4; if m=1, A is $C_1$–$C_{25}$alkyl, which is unsubstituted or substituted by $C_5$–$C_8$cycloalkyl; or $C_2$–$C_{25}$alkyl, which is interrupted by $C_5$–$C_8$cycloalkyl or one or more of the groups —S—, —O— and/or —$NR^2$—; or if m=1, A is $C_5$–$C_8$cycloalkyl, which is unsubstituted or substituted by $C_1$–$C_{12}$alkyl; $C_6$–$C_8$cycloalkenyl, which is unsubstituted or substituted by $C_1$–$C_{12}$alkyl; phenyl, which is unsubstituted or substituted by $C_1$–$C_{12}$alkyl; or $C_2$–$C_{25}$alkenyl; $C_7$–$C_{12}$phenylalkyl; or a group of the formula II

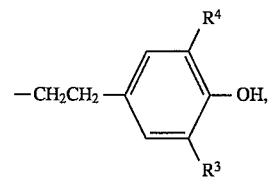

if m=2, A is a direct bond; $C_1$–$C_{12}$alkylene; $C_2$–$C_{12}$alkenylene; $C_5$–$C_8$cycloalkylene, which is unsubstituted or substituted by $C_1$–$C_{12}$alkyl; $C_6$–$C_8$cycloalkenylene, which is unsubstituted or substituted by $C_1$–$C_{12}$alkyl; phenylene; a divalent heterocyclic radical from the group comprising furan, thiophene or pyrrole, which is saturated on the nitrogen atom by hydrogen or the substituent —$R^2$; or, if m=2, A is $C_2$–$C_{18}$alkylene which is interrupted by $C_5$–$C_8$cycloalkylene or phenylene or at least one of the groups —S—, —O— or —$NR^2$—; and if m=3, A is $C_1$–$C_8$alkanetriyl; $C_2$–$C_8$alkenetriyl; benzenetriyl; a trivalent group of the formula

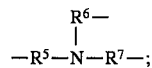

or $C_2$–$C_{18}$alkanetriyl, which is interrupted by at least one of the groups —S—,—O— or —$NR^2$—;

if m=4, A is a benzene or cyclohexyl radical having 4 free valencies;

$R^1$ and $R^{1'}$, independently of one another, are $C_1$–$C_{10}$alkyl or $C_5$–$C_8$cycloalkyl;

$R^2$ is H or $C_1$–$C_4$alkyl;

$R^3$ and $R^4$, independently of one another, are $C_1$–$C_4$alkyl; and $R^5$, $R^6$ and $R^7$, independently of one another, are $C_1$–$C_3$alkylene.

Compounds of the formula I in which $R^{1'}$ is tert-butyl or cyclohexyl and $R^1$ is methyl, tert-butyl or cyclohexyl;

n is a number from the range 4 to 6; and if m=1, A is $C_6$-$C_{18}$alkyl or $C_2$-$C_{12}$alkenyl;

if m=2, A is a direct bond; $C_1$-$C_{12}$alkylene; phenylene;

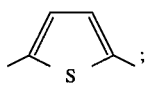

or $C_2$-$C_{36}$alkylene interrupted by 1 to 5 oxygen or sulfur atoms;

if m=3, A is benzenetriyl or a trivalent group of the formula

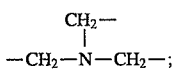

and if m=4, A is a benzene radical having 4 free valencies, are a particularly preferred subject.

Amongst these compounds, compounds of outstanding importance are those in which, if m=1, A is $C_2$-$C_{12}$alkenyl; and if m=2, A is phenylene;

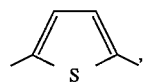

$C_2$-$C_{36}$alkylene interrupted by 1 to 5 oxygen atoms; or a group —$(CH_2)_k$—S—$(CH_2)_k$—; and k is an integer from the range from 1 to 3; and in particular the compounds in which m is 1 or 2.

Compounds of the formula I which are also particularly preferred are those in which n is an integer from the range from 5 to 8, in particular from the range 6 to 8 and especially 6.

Amongst the compounds of the formula I, compounds of the formula

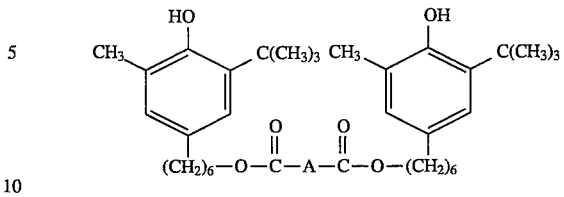

in which A is —$(CH_2)_j$—; —$(CH_2)_k$—S—$(CH_2)_k$—;

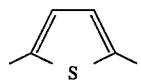

or
—$(CH_2)_2$—O—$[(CH_2)_2$—O—$]_j$—$(CH_2)_2$—hat; j is 0 or an integer from the range from 1 to 4; and k is an integer from the range from 1 to 3, are particularly outstanding.

The following compounds in particular are of outstanding importance:
a) 6-(3-tert-butyl-4-hydroxy-5-methylphenyl)hexyl stearate;
b) 6-(3,5-di-tert-butyl-4-hydroxyphenyl)hexyl stearate;
c) bis[6-(3-tert-butyl-4-hydroxy-5-methylphenyl)hexyl] succinate;
d) bis[6-(3-tert-butyl-4-hydroxy-5-methylphenyl)hexyl] adipate;
e) bis[6-(3-tert-butyl-4-hydroxy-5-methylphenyl)hexyl] suberate;
f) bis[6-(3-tert-butyl-4-hydroxy-5-methylphenyl)hexyl] isophthalate;
g) bis[6-(3,5-di-tert-butyl-4-hydroxyphenyl)hexyl] isophthalate;
h) tris[6-(3-tert-butyl-4-hydroxy-5-methylphenyl)hexyl] trimellitate;
j) tris[6-(3,5-di-tert-butyl-4-hydroxyphenyl)hexyl] trimellitate;
k) tris[6-(3-tert-butyl-4-hydroxy-5-methylphenyl)hexyl] trimesate; and
l) tris[6-(3,5-di-tert-butyl-4-hydroxyphenyl)hexyl] trimesate of the formulae

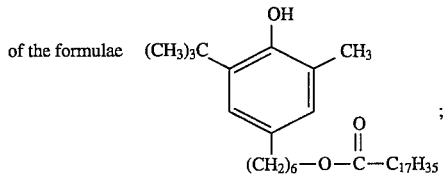 (a)

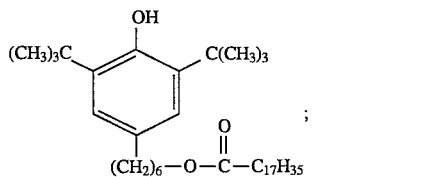 (b)

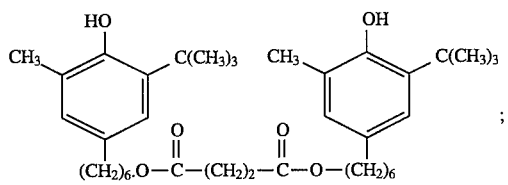 (c)

-continued
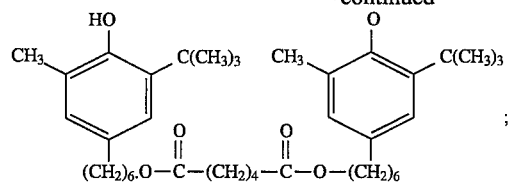 (d)
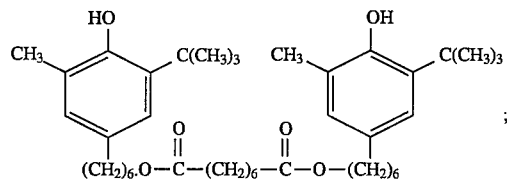 (e)
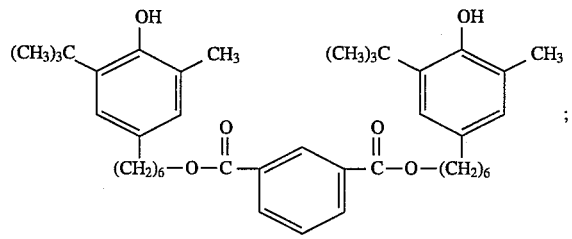 (f)
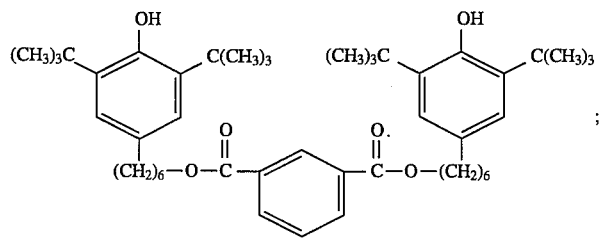 (g)
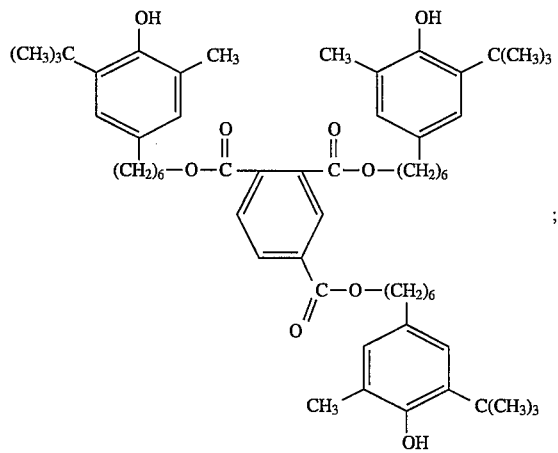 (h)

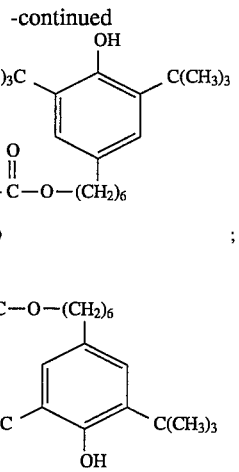
(j)

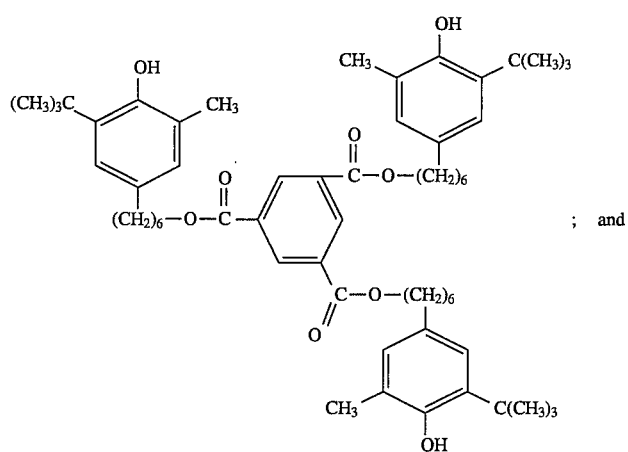
; and (k)

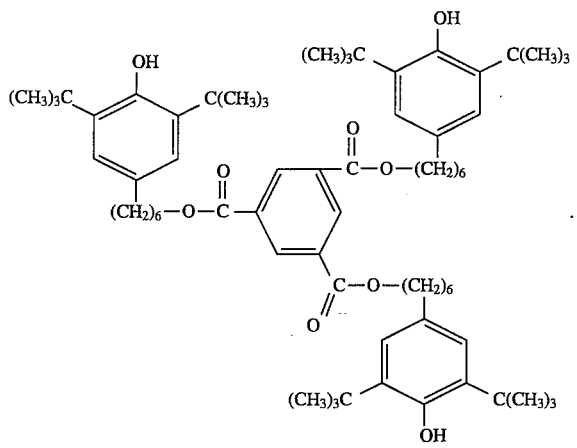

(l)

Compounds of the formula I in which n is an integer from the range 4 to 6; in particular those in which n is an integer from the range from 4 to 6 and in which, if m=1, A is $C_6$–$C_{20}$alkyl, if m=2, A is a direct bond, $C_1$–$C_{10}$alkylene, phenylene, or $C_2$–$C_6$alkylene interrupted by —S— and if m=3, A is benzenetriyl are of particular industrial importance.

A preferred subject of the invention also comprises compounds of the formula I in which m is 2 and A is $C_4$–$C_{36}$alkylene interrupted by at least one oxygen atom.

The compounds of the formula I in which, if m=1, A is $C_6$–$C_{20}$alkyl, $C_3$–$C_{18}$alkenyl, $C_6$–$C_{36}$alkyl interrupted by one or more —S— or —O— groups, cyclohexyl, cyclohexyl substituted by $C_1$–$C_4$alkyl, phenyl, phenyl substituted by $C_1$–$C_{12}$alkyl, or phenylalkyl having a total of 7 to 9 carbon atoms, if m=2, A is a direct bond, $C_1$–$C_{12}$alkylene, $C_2$–$C_{12}$alkenylene, phenylene, or $C_2$–$C_{36}$alkylene interrupted by a —S— or —O— group, and if m=3, A is $C_1$–$C_8$alkanetriyl, benzenetriyl, alkylbenzenetriyl of 7 to 10 carbon atoms, or

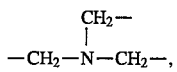

are also important.

The compounds of the formula I are suitable for stabilising organic materials against thermal, oxidative and actinic degradation. Reference is made in particular to their outstanding action as antioxidants in the stabilisation of organic materials.

Examples of such materials are:

1. polymers of monoolefins and diolefins, for example polypropylene, polyisobutylene, polybut-1-ene, poly-4-methylpent-1-ene, polyisoprene or polybutadiene and also polymers of cycloolefins, for example, of cyclopentene or norbornene; and also polyethylene (which can be crosslinked, if desired), for example high density polyethylene (HDPE), low density polyethylene (LDPE), linear low density polyethylene (LLDPE) or branched low density polyethylene (BLDPE).

Polyolefins, i.e. polymers of monoolefins, such as are mentioned by way of example in the preceding paragraph, in particular polyethylene and polypropylene, can be prepared by diverse processes, in particular by the following methods:

a) free radical polymerisation (usually at high pressure and high temperature).

b) by means of a catalyst, the catalyst usually containing one or more metals of groups IVb, Vb, VIb or VIII. These metals usually have one or more ligands, such as oxides, halides, alcoholates, esters, ethers, amines, alkyls, alkenyls and/or aryls, which can be either π- or σ-coordinated. These metal complexes can be free or fixed on a support, for example on activated magnesium chloride, titanium(II) chloride, aluminium oxide or silicon oxide. These catalysts can be soluble or insoluble in the polymerisation medium. The catalysts can be active as such in the polymerisation or further activators can be used, for example metal alkyls, metal hydrides, metal alkyl halides, metal alkyl oxides or metal alkyl oxanes, the metals being elements of groups Ia, IIa and/or IIIa. The activators can, for example, be modified by further ester, ether, amine or silyl ether groups. These catalyst systems are usually designated Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of various types of polyethylene (for example LDPE/HDPE).

3. Copolymers of monoolefins and diolefins with one another or with other vinyl monomers, for example ethylene-propylene copolymers, linear low density polyethylene (LLDPE) and mixtures thereof with low density polyethylene (LDPE), propylene-but-1-ene copolymers, propylene-isobutylene copolymers, ethylene-but-1-ene copolymers, ethylene-hexene copolymers, ethylene-methylpentene copolymers, ethylene-heptene copolymers, ethylene-octene copolymers, propylene-butadiene copolymers, isobutylene-isoprene copolymers, ethylene-alkyl acrylate copolymers, ethylene-alkyl methacrylate copolymers, ethylene-vinyl acetate copolymers and their copolymers with carbon monoxide, or ethylene-acrylic acid copolymers and their salts (ionomers), and also terpolymers of ethylene with propylene and a diene, such as hexadiene, dicyclopentadiene or ethylidenenorbornene; and also mixtures of such copolymers with one another and with polymers mentioned under 1 ), for example polypropylene/ethylene-propylene copolymers, LDPE/ethylene-vinyl acetate copolymers, LDPE/ethylene acrylic acid copolymers, LLDPE/ethylene-vinyl acetate copolymers, LLDPE/ethylene-acrylic acid copolymers and alternating or randomly composed polyalkylene/carbon monoxide copolymers and mixtures thereof with other polymers, for example polyamides.

4. Hydrocarbon resins (for example $C_5$–$C_9$) including hydrogenated modifications thereof (for example tackifier resins) and mixtures of polyalkylenes and starch.

5. Polystyrene, poly(p-methylstyrene),and poly(α-methylstyrene).

6. Copolymers of styrene or α-methylstyrene with dienes or acrylic derivatives, for example styrene-butadiene, styrene-acrylonitrile, styrene-alkyl methacrylate, styrene-butadiene-alkyl acrylate and -alkyl methacrylate, styrene-maleic anhydride and styrene-acrylonitrile-methyl acrylate; mixtures of high impact strength composed of styrene copolymers and another polymer, for example a polyacrylate, a diene polymer or an ethylene-propylene-diene terpolymer; and also block copolymers of styrene, for example styrene-butadiene-styrene, styrene-isoprene-styrene, styrene-ethylene/butylene-styrene or styrene-ethylene/propylene-styrene.

7. Graft copolymers of styrene or α-methylstyrene, for example styrene on polybutadiene, styrene on polybutadiene-styrene or polybutadiene-acrylonitrile copolymers, styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene, styrene and alkyl acrylates or alkyl methacrylates on polybutadiene, styrene and acrylonitrile on ethylene-propylene-diene terpolymers, styrene and acrylonitrile on polyalkyl acrylates or polyalkyl methacrylates, styrene and acrylonitrile on acrylate-butadiene copolymers, and also their mixtures with the copolymers mentioned under 6), as are known, for example, as so-called ABS, MBS, ASA or AES polymers.

8. Halogen-containing polymers, for example polychloroprene, chlorinated rubber, chlorinated or chlorosulfonated polyethylene, copolymers of ethylene and chlorinated ethylene, epichlorohydrin homopolymers and copolymers, in particular polymers of halogen-containing vinyl compounds, for example polyvinyl chloride, polyvinylidene chloride, polyvinyl fluoride or polyvinylidene fluoride; and also their copolymers, such as vinyl chloride-vinylidene chloride, vinyl chloride-vinyl acetate or vinylidene chloride-vinyl acetate.

9. Polymers which are derived from α,β-unsaturated acids and their derivatives, such as polyacrylates and polymethacrylates, polymethyl methacrylates impact-modified with butyl acrylate, polyacrylamide and polyacrylonitrile.

10. Copolymers of the monomers mentioned under 9), with one another or with other unsaturated monomers, for example acrylonitrile-butadiene copolymers, acrylonitrile-alkyl acrylate copolymers, acrylonitrile-alkoxyalkyl acrylate copolymers, acrylonitrile-vinyl halide copolymers or acrylonitrile-alkyl methacrylate-butadiene terpolymers.

11. Polymers which are derived from unsaturated alcohols and amines or their acyl derivatives or acetals, such as polyvinyl alcohol, polyvinyl acetate, polyvinyl stearate, polyvinyl benzoate, polyvinyl maleate, polyvinyl butyral, polyallyl phthalate and polyallyl melamine; and also their copolymers with olefins mentioned under point 1.

12. Homopolymers and copolymers of cyclic ethers, such as polyalkylene glycols, polyethylene oxide, polypropylene oxide or their copolymers with bisglycidyl ethers.

13. Polyacetals, such as polyoxymethylene, and also those polyoxymethylenes which contain comonomers, for example ethylene oxide; polyacetals which are modified with thermoplastic polyurethanes, acrylates or MBS.

14. Polyphenylene oxides and polyphenylene sulfides and their mixtures with styrene polymers or polyamides.

15. Polyurethanes which are derived from polyethers, polyesters and polybutadienes having terminal hydroxyl groups on the one hand and aliphatic or aromatic polyisocyanates on the other hand, and their precursors.

16. Polyamides and copolyamides which are derived from diamines and dicarboxylic acids and/or from aminocarboxylic acids or the corresponding lactams, such as polyamide 4, polyamide 6, polyamide 6/6, 6/10, 6/9, 6/12, 4/6 and 12/12, polyamide 11, polyamide 12 and aromatic polyamides based on m-xylene, diamine and adipic acid; polyamides prepared from hexamethylenediamine and isophthalic acid and/or terephthalic acid and, if desired, an elastomer as modifier, for example poly-2,4,4-trimethylhexamethyleneterephthalamide or poly-m-phenyleneisophthalamide. Block copolymers of the abovementioned polyamides with polyolefins, olefin copolymers, ionomers or chemically bonded or grafted elastomers; or with polyethers, for example with polyethylene glycol, polypropylene glycol or polytetramethylene glycol. And also polyamides or copolyamides modified with EPDM or ABS; and also polyamides condensed during processing ("RIM polyamide systems").

17. Polyureas, polyimides, polyamide-imides and polybenzimidazoles.

18. Polyesters which are derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate, and polyhydroxybenzoates, and also block polyether-esters which are derived from polyethers having hydroxyl end groups; and also polyesters modified with polycarbonates or MBS.

19. Polycarbonates and polyester-carbonates.

20. Polysulfones, polyether-sulfones and polyether-ketones.

21. Crosslinked polymers which are derived from aldehydes on the one hand and phenols, urea or melamine on the other hand, such as phenol-formaldehyde resins, urea-formaldehyde resins and melamine-formaldehyde resins.

22. Drying and non-drying alkyd resins.

23. Unsaturated polyester resins which are derived from copolyesters of saturated and unsaturated dicarboxylic acids with polyhydric alcohols and also vinyl compounds as crosslinking agents, and also their halogen-containing modifications of low flammability.

24. Crosslinkable acrylic resins which are derived from substituted acrylic acid esters, for example from epoxy acrylates, urethane acrylates or polyester acrylates.

25. Alkyd resins, polyester resins and acrylate resins which are crosslinked with melamine resins, urea resins, polyisocyanates or epoxy resins.

26. Crosslinked epoxy resins which are derived from polyepoxides, for example from bis-glycidyl ethers or from cycloaliphatic diepoxides.

27. Naturally occurring polymers, such as cellulose, natural rubber, gelatin, and also their polymer-homologous chemically modified derivatives, such as cellulose acetates, cellulose propionates and cellulose butyrates, or cellulose ethers, such as methylcellulose; and also colophony resins and derivatives.

28. Mixtures (polyblends) of the abovementioned polymers, for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylate, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

29. Naturally occurring and synthetic organic substances which are pure monomer compounds or mixtures of such compounds, for example mineral oils, animal or vegetable fats, oils and waxes, or oils, waxes and fats based on synthetic esters (for example phthalates, adipates, phosphates or trimellitates), and also admixtures of synthetic esters with mineral oils in arbitrary proportions by weight, such as are used, for example, as spinning preparations, and also aqueous emulsions thereof.

30. Aqueous emulsions of naturally occurring or synthetic rubbers, for example natural rubber latex or latexes of carboxylated styrene-butadiene copolymers.

Further subjects of the invention are, therefore, compositions containing an organic material sensitive to oxidative, thermal and/or actinic degradation and at least one compound of the formula I, as well as the use of compounds of the formula I for stabilising organic material against oxidative, thermal or actinic degradation.

The invention therefore also comprises a method for stabilising organic material against thermal, oxidative and/or actinic degradation, which method comprises adding at least one compound of the formula I to said material.

The use of compounds of the formula I as antioxidants in synthetic organic polymers is of particular interest.

Preferred organic materials are polymers, for example synthetic organic polymers or mixtures of such polymers, in particular thermoplastic polymers. Particularly preferred organic materials are polyolefins and styrene copolymers, for example those indicated above under points 1 to 3 and under points 5 and 6, in particular polyethylene and polypropylene and also ABS and styrene-butadiene copolymers. Compositions in which the organic material is a synthetic organic polymer or a mixture of such polymers, in particular a polyolefin or a styrene copolymer, are therefore a preferred subject of the invention.

In general, the compounds of the formula I are added to the material to be stabilised in amounts of from 0.01 to 10 %, preferably 0.01 to 5 % and in particular 0.01 to 2 %, with respect to the total weight of the material to be stabilised. The use of the compounds according to the invention in amounts of from 0.01 to 0.5 %, in particular 0.05 to 0.3 %, is particularly preferred.

In addition to the compounds of the formula I, the compositions according to the invention can additionally contain conventional additives, for example those indicated below.

1. Antioxidants 1.1. alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-di-cyclopentyl-4-methylphenol, 2-(α-methylcyclohexyl)- 4,6-dimethylphenol, 2,6-di-octadecyl-4-methylphenol, 2,4,6-tricyclohexylphenol, 2,6-di-tert-butyl-4-methoxymethylphenol, 2,6-di-nonyl-4-methylphenol, 2,4-dimethyl- 6-(1'-methyl-undec-1'-yl)phenol, 2,4-dimethyl-6-(1'-methyl-heptadec-1'-yl)phenol, 2,4-di-methyl- 6-(1'-methyl-tridec-1'-yl)phenol and mixtures thereof.

1.2. Alkylthiomethylphenols, for example 2,4-di-octylthiomethyl-6-tert-butylphenol, 2,4-di-octylthiomethyl-6-methylphenol, 2,4-di-octylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butyl-hydroquinone, 2,5-di-tert-amyl-hydroquinone, 2,6-diphenyl-4-octadecyloxyphenol, 2,6-di-tert-butyl-hydroquinone, 2,5-di-tert-butyl-4-hydroxyanisole, 3,5-di-tert-butyl-4-hydroxyanisole, 3,5-di-tert-butyl-4-hydroxyphenyl stearate, and bis(3,5-di-tert-butyl-4-hydroxyphenyl) adipate.

1.4. Hydroxylated thiodiphenyl ethers, for example 2,2'-thiobis(6-tert-butyl-4-methylphenol), 2,2'-thio-bis(4-octylphenol), 4,4'-thio-bis(6-tert-butyl-3-methylphenol), 4,4'-thio-bis(6-tert-butyl-2-methylphenol), 4,4'-thio-bis(3,6-di-sec-amylphenol) and 4,4'-bis(2,6-dimethyl-4-hydroxyphenyl) disulfide.

1.5. Alkylidene-bisphenols, for example 2,2'-methylene-bis(6-tert-butyl-4-methylphenol), 2,2'-methylene-bis(6-tert-butyl-4-ethylphenol), 2,2'-methylene-bis[4-methyl- 6-(α-methylcyclohexyl)phenol], 2,2'-methylene-bis(4-methyl-6-cyclohexylphenol), 2,2'-methylenebis(6-nonyl-4-methylphenol), 2,2'-methylene-bis(4,6-di-tert-butylphenol), 2,2'-ethylidene-bis( 4,6-di-tert-butylphenol), 2,2'-ethylidene-bis(6-tert-butyl-4-isobutylphenol), 2,2'-methylene-bis[6-(α-methylbenzyl)-4-nonylphenol], 2,2'-methylene-bis[ 6-(α,α-di-methylbenzyl)- 4-nonylphenol], 4,4'-methylene-bis(2,6-di-tert-butylphenol), 4,4'-methylene-bis (6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris( 5-tert-butyl-4-hydroxy-2-methylphenyl)butane, 1,1-bis(5-tert-butyl-4-hydroxy- 2-methylphenyl)- 3-n-dodecylmercaptobutane, ethylene glycol bis[3,3-bis(3'-tert-butyl-4'-hydroxyphenyl)butyrate]bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl] terephthalate, 1,1-bis(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane and 1,1,5,5-tetra(5-tert-butyl-4-hydroxy-2-methylphenyl)pentane.

1.6. O-, N- and S-benzyl compounds, for example 3,5,3',5'-tetra-tert-butyl-4,4'-dihydroxydibenzyl ether, octadecyl 4-hydroxy-3,5-dimethylbenzylmercaptoacetate, tris( 3,5-di-tert-butyl- 4-hydroxybenzyl)amine, bis(4-tert-butyl-3-hydroxy-2,6-dimethylbenzyl) dithioterephthalate, bis(3,5-di-tert-butyl-4-hydroxybenzyl) sulfide, and isooctyl 3,5-di-tert-butyl-4-hydroxybenzylmercaptoacetate.

1.7. Hydroxybenzylated malonates, for example dioctadecyl 2,2-bis(3,5-di-tert-butyl-2-hydroxybenzyl)malonate, di-octadecyl 2-(3-tert-butyl-4-hydroxy-5-methylbenzyl)malonate, di-dodecylmercaptoethyl 2,2-bis(3,5-di-tert-butyl-4-hydroxybenzyl)malonate, di[ 4( 1,1,3,3-tetramethylbutyl)phenyl] 2,2-bis(3,5-di-tert-butyl-4-hydroxybenzyl)malonate.

1.8. Hydroxybenzyl-aromatic compounds, for example 1,3,5-tris(3,5-di-tert-butyl-4-hydroxybenzyl)-2,4,6-trimethylbenzene, 1,4-bis(3,5-di-tert-butyl- 4-hydroxybenzyl)-2,3,5,6-tetramethylbenzene, 2,4,6-tris(3,5-di-tert-butyl- 4-hydroxybenzyl)phenol.

1.9. Triazine compounds, for example 2,4-bis-octylmercapto-6-(3,5-di-tert-butyl-4-hydroxyanilino)-1,3,5-triazine, -octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl- 4-hydroxybenzyl) isocyanurate, 1,3,5-tris(4-tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl) hexahydro-1,3,5-triazine and 1,3,5-tris(3,5-dicyclohexyl-4-hydroxybenzyl) isocyanurate.

1.10. Benzylphosphonates, for example dimethyl 2,5-di-tert-butyl-4-hydroxybenzylphosphonate, diethyl 3,5-di-tert-butyl-4-hydroxybenzylphosphonate, dioctadecyl 3,5-di-tert-butyl-4-hydroxybenzylphosphonate, dioctadecyl 5-tert-butyl-4-hydroxy-3-methylbenzylphosphonate and the calcium salt of monoethyl 3,5-di-tert-butyl-4-hydroxybenzylphosphonate.

1.11. Acylaminophenols, for example 4-hydroxylauric acid anilide, 4-hydroxystearic acid anilide and octyl N-(3, 5-di-tert-butyl-4-hydroxyphenyl)carbamate.

1.12. Esters of 1β-(3,5-di-tert-butyl-4-hydroxyphenyl) propionic acid with monohydric or polyhydric alcohols, for example with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalic acid diamide, 3-thiaundecanol, 3-thiapentadecanol, trimethylhexanediol, trimethylolpropane and 4-hydroxymethyl-1-phospha-2,6,7-trioxabicyclo[2.2.2 ]octane.

1.13. Esters of β-(5-tert-butyl-4-hydroxy-3-methylphenyl)propionic acid with monohydric or polyhydric alcohols, for example methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxy)ethyl isocyanurate, N,N'-bis(hydroxyethyl)oxalic acid diamide, 3-thiaundecanol, 3-thiapentadecanol, trimethylhexanediol, trimethylolpropane and 4-hydroxymethyl-1-phospha-2,6,7-trioxabicyclo[ 2.2.2 ]octane.

1.14. Esters of β-(3,5-dicyclohexyl-4-hydroxyphenyl) propionic acid with monohydric or polyhydric alcohols, for example with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxy)ethyl isocyanurate, N,N'-bis(hydroxyethyl)oxalic acid diamide, 3-thiaundecanol, 3-thiapentadecanol, trimethylhexanediol, trimethylolpropane and 4-hydroxymethyl-1-phospha-2,6,7-trioxabicyclo[2.2.2]octane.

1.15. Esters of 3,5-di-tert-butyl-4-hydroxyphenylacetic acid with monohydric or polyhydric alcohols, for example methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxy)ethyl isocyanurate, N,N'-bis(hydroxyethyl)oxalic acid diamide, 3-thiaundecanol, 3-thiapentadecanol, trimethylhexanediol, trimethylolpropane and 4-hydroxymethyl-1-phospha-2,6,7-trioxabicyclo[2.2.2]octane.

1.16. Amides of β-(3,5-di-tert-butyl-4-hydroxyphenyl) propionic acid, for example N,N'-bis(3,5-di-tert-butyl-4-hydroxyphenylpropionyl)hexamethylenediamine, N,N'-bis(3, 5-di-tert-butyl-4-hydroxyphenylpropionyl)trimethylenediamine and N,N'-bis(3,5-di-tert-butyl-4-hydroxyphenylpropionyl)hydrazine.

2. UV-absorbers and light stabilisers 2.1.2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tertbutyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octoxyphenyl)benzotriazole, 2-(3',5'-di-tert-amyl-2'-hydroxyphenyl)benzotriazole, 2-(3',5'-bis(α,α-dimethylbenzyl)-2'-hydroxyphenyl)benzotriazole, a mixture of 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazol-2-ylphenol]; the transesterification product of 2-[3'-tert-butyl-5'-(2-methoxycarbonylethyl)-2'-hydroxyphenyl]benzotriazole with polyethylene glycol 300; [R—CH$_2$CH$_2$—COO(CH$_2$)$_3$]$_2$, where R=3'-tert-butyl-4'-hydroxy-5'-2H-benzotriazol-2-ylphenyl.

2.2. 2-Hydroxybenzophenone, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivative.

2.3. Esters of substituted or unsubstituted benzoic acids, for example 4-tertbutyl-phenyl salicylate, phenyl salicylate, octylphenyl salicylate, dibenzoylresorcinol, bis(4-tert-butylbenzoyl)resorcinol, benzoylresorcinol, 3,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate and 2-methyl-4,6-di-tert-butylphenyl 3,5-di-tert-butyl-4-hydroxybenzoate.

2.4. Acrylates, for example ethyl and isooctyl α-cyano-β,β-diphenylacrylate, methyl α-carbomethoxycinnamate, methyl and butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis[4-(1,1,3,3-tetramethylbutyl)phenol], such as the 1:1 or 1:2 complex, if desired with additional ligands, such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, such as of the methyl or ethyl ester, nickel complexes of ketoximes, such as of 2-hydroxy-4-methylphenylundecylketoxime and nickel complexes of 1-phenyl-4-lauroyl-5-hydroxypyrazole, if desired with additional ligands.

2.6. Sterically hindered amines, for example bis(2,2,6,6-tetramethylpiperidyl) sebacate, bis(2,2,6,6-tetramethylpiperidyl) succinate, bis(1,2,2,6,6-pentamethylpiperidyl) sebacate, bis(1,2,2,6,6-pentamethylpiperidyl) n-butyl-3,5-di-tert-butyl-4-hydroxybenzylmalonate, the condensation product of 1-hydroxyethyl-2,2,6,6-tetramethyl-4-hydroxypiperidine and succinic acid, the condensation product of N,N'-bis(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl) nitrilotriacetate, tetrakis(2,2,6,6-tetramethyl-4-piperidyl) 1,2,3,4-butanetetraoate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl) 2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl) sebacate, bis(1-octyloxy-2,2,6,6-tetramethylpiperidyl) succinate, the condensation product of N,N'-bis(2,2,6,6-tetramethyl4-piperidyl)hexamethylenediamine and 4-morpholino-2,6-dichloro-1,3,5-triazine, the condensation product of 2-chloro-4,6-di(4-n-butylamino-2,2,6,6-tetramethylpiperidyl)1,3,5-triazine and 1,2-bis(3-aminopropylamino)ethane, the condensation product of 2-chloro-4,6-di(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione and 3-dodecyl-1-(1,2,2,6,6-pentamethyl-4-piperidyl)pyrrolidine-2,5-dione.

2.7. Oxalic acid diamides, for example 4,4'-dioctyloxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxalamide, 2-ethoxy-5-tert-butyl-2'-ethyloxanilide and its mixture with 2-ethoxy-2'-ethyl-5,4'-di-tert-butyloxanilide, and mixtures of o- and p-methoxy- and also of o- and p-ethoxy-disubstituted oxanilides.

2.8.2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butyloxypropyloxy)phenyl]-4,6-bis(2,4-dimethylphenyl)-1,3,5-triazine, 2-[2-hydroxy-4-(2-hydroxy-3-octyloxypropyloxy)phenyl]-4,6-bis(2,4-dimethylphenyl)-1,3,5-triazine.

3. Metal deactivators, for example N,N'-diphenyloxalic acid diamide, N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalic acid dihydrazide, oxanilide, isophthalic acid dihydrazide, sebacic acid bis-phenylhydrazide, N,N'-diacetyladipic acid dihydrazide, N,N'-bis-salicyloyloxalic acid dihydrazide, and N,N'-bis-salicyloylthiopropionic acid dihydrazide.

4. Further phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearylpentaerythritol diphosphite, tris(2,4-di-tert-butylphenyl) phosphite, diisodecylpentaerythritol diphosphite, bis(2,4-di-tert-butylphenyl) pentaerythritol diphosphite, bis(2,6-di-tert-butyl-4-methylphenyl)pentaerythritol diphosphite, bis-isodecyloxypentaerythritol diphosphite, bis(2,4-di-tert-butyl-6-methylphenyl)pentaerythritol diphosphite, bis(2,4,6-tri-tert-butylphenyl)pentaerythritol diphosphite, tristearylsorbitol triphosphite, tetrakis(2,4-di-tert-butylphenyl)4,4'-biphenylenediphosphonite, 6-isooctyloxy- 2,4,8,10-tetra-tert-butyl- 12H-dibenz[d,g]-1,3,2-dioxaphosphocin and 6-fluoro-2,4,8,10-tetra-tert-butyl- 12-methyldibenz[d,g]-1,3,2-dioxaphosphocin, bis(2,4-di-tert-butyl-6-methylphenyl) methyl phosphite and bis(2,4-di-tert-butyl-6-methylphenyl) ethyl phosphite.

5. Peroxide-destroying compounds, for example esters of β-thiodipropionic acid, for example the lauryl, stearyl, myristyl or tridecyl ester, mercaptobenzimidazole, the zinc salt of 2-mercaptobenzimidazole, zinc dibutyldithiocarbamate, dioctadecyl disulfide and pentaerythritol tetrakis(β-dodecylmercapto)propionate.

6. Polyamide stabilisers, for example copper salts in combination with iodides and/or phosphorus compounds and salts of divalent manganese.

7. Basic costabilisers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate, potassium palmitate, antimony pyrocatechinate or tin pyrocatechinate.

8. Nucleating agents, for example 4-tert-butylbenzoic acid, adipic acid and diphenyl acetic acid.

9. Fillers and reinforcing agents, for example calcium carbonate, silicates, glass fibres, asbestos, talc, kaolin, mica, barium sulfate, metal oxides and metal hydroxides, carbon black and graphite.

10. Other additives, for example plasticisers, lubricants, emulsifiers, pigments, fluorescent whitening agents, flameproofing agents, antistatic agents and propellants.

11. Benzofuranones and indolinones, as described, for example, in U.S. Pat. No. 4,325,863 or U.S. Pat. No. 4,338,244.

The conventional additives are added, for example, in concentrations of from 0.01 to 10%, with respect to the total weight of the material to be stabilised.

The incorporation of the compound of the formula I and, if desired, further additives in the organic material is effected by known methods. Incorporation into the materials can, for example, be effected by mixing in or applying the compounds of the formula I and, if desired, further additives using the methods customary in the art. If the materials are polymers, in particular synthetic polymers, the incorporation can be effected before or during shaping, or by applying the dissolved or dispersed compounds to the polymer, with subsequent evaporation of the solvent where appropriate. In the case of elastomers, these can also be stabilised as latexes. A further possibility for incorporating the compounds of the formula I in polymers comprises adding said compounds before, during or immediately following the polymerisation of the corresponding monomers or prior to crosslinking. The compounds of the formula I can be added as such, but also in encapsulated form (for example in waxes, oils or polymers). In the case of addition before or during the polymerisation, the compounds of the formula I can also act as regulators for the chain length of the polymers (chain stoppers).

The compounds of the formula I can also be added to the materials to be stabilised in the form of a masterbatch which contains said compounds, for example in a concentration of from 2.5 to 25% by weight.

The materials stabilised in this way can be used in very diverse forms, for example in the form of films, fibres, tapes, moulding compositions or sections or as binders for coating compositions, adhesives or putties.

The following examples further illustrate the invention. Unless indicated otherwise, parts and percentage data in these examples are by weight. In the formulae the prefix n designates a straight-chain alkyl radical and the prefix i a mixture of isomers. "Melting point" is abbreviated as "m.p." in the tables.

EXAMPLE 1a

Preparation of 4-(3-tert-butyl-5-methyl-4-hydroxyphenyl)butanol. 50 g of potassium hydroxide, 316 g of 2-tert-butyl-6-methylphenol and 866 g of 1,4-butanediol are initially introduced into an autoclave. After introducing nitrogen gas, the autoclave is closed and the mixture is heated at 235° C. (4 bar) for 6 hours, with stirring; a further rise in pressure as a consequence of the reaction is prevented by blowing of gas. When the reaction is complete, the reaction mixture is cooled to 80° C. and the autoclave is emptied. Excess butanediol is removed by distillation. The distillation residue is poured into 1 l of water and 500 ml of toluene. The organic phase is then washed with water until neutral and the toluene is stripped off by applying a vacuum. The remaining residue (310 g) contains 68–70% of the title product of the formula

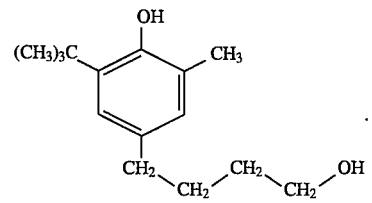

Further purification is effected by fractional distillation under vacuum; the pure product boils at 115° C. and 35 Pa (=0.35 mbar). It has a refractive index $n_{20}^D$ of 1.5322.

EXAMPLE 1b

Preparation of 6-(3-tert-butyl-5-methyl-4-hydroxyphenyl)hexanol. Example 1a is repeated except that in place of 1,4-butanediol an equivalent amount of 1,6-hexanediol is used. The resulting product of the formula

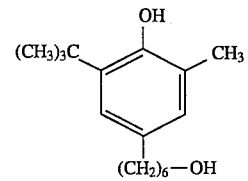

has a boiling point at 35 Pa (=0.35 mbar) of 135° C. and melts at 45° C.

EXAMPLE 1c

A solution of 25.5 g (84 mmol) of stearoyl chloride in 10 ml of toluene is added dropwise at 10° C., under nitrogen, to a solution of 18.9 g (80 mmol) of 4-(3-tert-butyl-5-methyl-4-hydroxyphenyl)butanol (product from Example 1a) and 9.5 g (120 mmol) of pyridine in 90 ml of toluene. The white suspension is then allowed to warm to 20°–25° C. and filtered and the filtrate is poured into approximately 1 molar aqueous HCl and extracted with ethyl acetate. After drying and concentrating the organic phase, the resulting crude product is purified by chromatography (SiO₂; hexane-:ethyl acetate=19:1). 37.2 g (93%) of the product of the formula

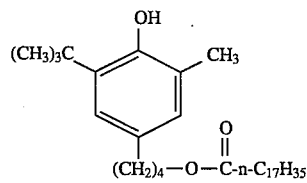

(compound No. 1) are obtained in the form of a colourless liquid. Characterisation (IR) and analysis are given in Table 1.

EXAMPLES 2–16

In order to prepare compounds Nos. 2 to 16, corresponding ω-(3-tert-butyl-5-methyl-4-hydroxyphenyl)alkanols or ω-(3,5-di-tert-butyl-4-hydroxyphenyl)alkanols are first synthesised by the method described in Example 1a. The starting compounds (compounds of the formula IV) thus obtained are then reacted using corresponding acid chlorides in accordance with the method described in Example 1c to give the said end products (compounds of the formula I). Data on the purity and characterisation of the compounds are summarised in Tables 1 and 2. Where no melting point is indicated, the compounds are liquid at room temperature.

TABLE 1

Analytical and IR data for compounds Nos. 1–8

Compound type:

$$\text{(CH}_3)_3\text{C} - \underset{\underset{(CH_2)_n-O-\overset{O}{\overset{\|}{C}}-A}{}}{\overset{OH}{\bigcirc}} - CH_3$$

| Compound No. | n | A | ANALYSIS: % C: calc. | % C: found | % H: calc. | % H: found | IR: 1/λ C=O [cm$^{-1}$] |
|---|---|---|---|---|---|---|---|
| 1 | 4 | -n-C$_{17}$H$_{35}$ | 78.8 | 78.7 | 11.6 | 11.4 | 1738 |
| 2 | 4 | -n-C$_{7}$H$_{15}$ | 76.2 | 76.1 | 10.6 | 10.6 | 1719 |
| 3 | 4 | -i-C$_{7}$H$_{15}$ | 76.2 | 76.2 | 10.6 | 11.0 | 1717 |
| 4 | 4 | -i-C$_{12}$H$_{25}$ | 77.7 | 77.7 | 11.2 | 11.1 | 1717 |
| 5 | 4 | —CH$_2$—CH(C$_2$H$_5$)—CH$_2$—C$_2$H$_5$ | 76.2 | 76.0 | 10.6 | 10.4 | 1715 |
| 6 | 6 | —CH$_2$—CH(C$_2$H$_5$)—CH$_2$—C$_2$H$_5$ | 76.9 | 76.9 | 10.8 | 10.6 | 1715 |
| 7 | 6 | -n-C$_{11}$H$_{23}$ | 78.0 | 77.9 | 11.3 | 11.5 | 1732 |
| 8 | 6 | -n-C$_{17}$H$_{35}$ | 79.2 | 79.1 | 11.8 | 12.2 | 1720 |

TABLE 2

Melting points, analytical and IR data for compounds Nos. 9–16

Compound type:

$$\text{(CH}_3)_3\text{C} - \underset{\underset{(CH_2)_n-O-\overset{O}{\overset{\|}{C}}-A}{}}{\overset{OH}{\bigcirc}} - C(CH_3)_3$$

| Compound No. | n | A | m.p.[°C.] | % C: calc. | % C: found | % H: calc. | % H: found | IR: 1/λ C=O [cm$^{-1}$] |
|---|---|---|---|---|---|---|---|---|
| 9 | 4 | —CH$_2$—CH(C$_2$H$_5$)—CH$_2$—C$_2$H$_5$ | — | 77.2 | 77.0 | 11.0 | 10.8 | 1732 |
| 10 | 4 | -n-C$_{7}$H$_{15}$ | — | 77.2 | 77.2 | 11.0 | 11.4 | 1736 |
| 11 | 4 | -i-C$_{12}$H$_{25}$ | — | 78.4 | 78.3 | 11.5 | 11.5 | 1735 |
| 12 | 4 | -n-C$_{17}$H$_{35}$ | 30–33 | 79.4 | 79.5 | 11.8 | 12.1 | 1738 |
| 13 | 5 | -n-C$_{17}$H$_{35}$ | 31–32 | 79.5 | 79.6 | 11.9 | 11.9 | 1738 |

TABLE 2-continued

Melting points, analytical and IR data for compounds Nos. 9–16

Compound type:

(CH₃)₃C—[phenol ring with OH]—C(CH₃)₃
(CH₂)ₙ—O—C(=O)—A

| Compound No. | n | A | m.p.[°C.] | % C: calc. | % C: found | % H: calc. | % H: found | IR: 1/λ C=O [cm⁻¹] |
|---|---|---|---|---|---|---|---|---|
| 14 | 6 | —CH₂—CH(C₂H₅)—CH₂—C₂H₅ | — | 77.7 | 77.7 | 11.2 | 11.5 | 1738 |
| 15 | 6 | -n-C₁₁H₂₃ | — | 78.6 | 78.5 | 11.6 | 11.9 | 1737 |
| 16 | 6 | -n-C₁₇H₃₅ | 35 | 79.7 | 79.6 | 12.0 | 12.2 | 1738 |

EXAMPLE 17

13.6 g (0.074 mol) of adipic acid dichloride are added dropwise at 10° C. under nitrogen to a colourless solution of 33 g (0.14 mol) of the product from Example 1a and 16.6 g (0.21 mol) of pyridine in 200 ml of toluene in a 350 ml sulfonation flask. The mixture is then allowed to warm to room temperature, while continuing to stir. After 2 h the reaction mixture is poured into aqueous hydrochloric acid and extracted with ethyl acetate. After drying and concentrating the organic phase, the resulting crude product is purified by chromatography (SiO₂; hexane:ethyl acetate= 19:1). 36 g (88%) of the product (compound No. 17) of the formula

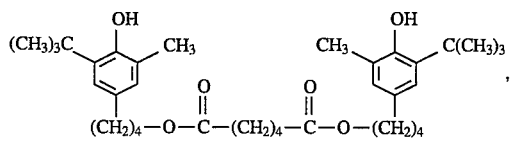

which has a melting point of 50°–52° C., are obtained. Characterisation (IR) and analysis are given in Table 3.

EXAMPLES 18–22 and 24–34

In order to prepare compounds Nos. 18 to 22 and 24 to 34, corresponding ω-(3-tert-butyl-5-methyl-4-hydroxyphenyl)alkanols or ω-(3,5-di-tert-butyl-4-hydroxyphenyl)alkanols are first synthesised by the method described in Example 1a. The starting compounds (compounds of the formula IV) thus obtained are then reacted using corresponding dicarboxylic acid dichlorides in accordance with the method described in Example 1c to give the said end products (compounds of the formula I). Data on the purity and characterisation of the resulting compounds are summarised in Tables 3, 4 and 5.

EXAMPLE 23

4.98 g (30 mmol) of isophthalic acid, 14.4 g (70 mmol= 2.3 equivalents) of dicyclohexylcarbodiimide and 150 ml of dichloromethane are mixed at 20°–25° C. under nitrogen in a 750 ml sulfonation flask. A solution of 15.9 g (60 mmol=2 equivalents) of 6-(3-tert-butyl-5-methyl-4-hydroxyphenyl)-hexanol (product from Example 1b) in 80 ml of dichloromethane and a solution of 0.73 g (6 mmol) of dimethylaminopyridine in 5 ml of dichloromethane are added to the resulting white suspension. The mixture is refluxed for 4 hours. It is then cooled to 20°–25° C. and filtered and the filtrate is evaporated. The resulting crude product (viscous oil) is purified by chromatography (SiO₂; hexane/ethyl acetate=19/1). 11.3 g (57%) of compound No. 23 are obtained in the form of a colourless oil. Data on the purity and characterisation are given in Table 3.

TABLE 3

Melting points, analytical and IR data for compounds Nos. 17–23

Compound type:

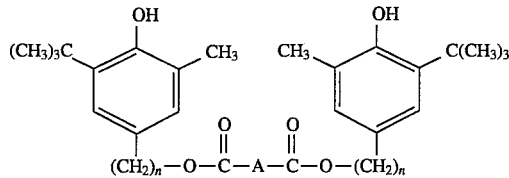

| Compound | | | | ANALYSIS: | | | | IR: 1/λ |
|---|---|---|---|---|---|---|---|---|
| | | | | % C: | | % H: | | |
| No. | n | A | m.p.[°C.] | calc. | found | calc. | found | C=O [cm⁻¹] |
| 17 | 4 | —(CH$_2$)$_4$— | 50-52 | 74.2 | 73.8 | 09.3 | 09.5 | 1718 |
| 18 | 4 | —(CH$_2$)$_8$— | — | 75.2 | 74.7 | 09.8 | 09.9 | 1717 |
| 19 | 6 | — | — | 74.2 | 74.1 | 09.3 | 09.7 | 1738 |
| 20 | 6 | —(CH$_2$)$_2$— | 90–103 | 74.7 | 73.9 | 09.6 | 09.8 | 1713 |
| 21 | 6 | —(CH$_2$)$_4$— | 91–95 | 75.2 | 75.0 | 09.8 | 09.7 | 1718 |
| 22 | 6 | —(CH$_2$)$_8$— | — | 76.0 | 75.5 | 10.2 | 10.2 | 1718 |
| 23 | 6 | (phenylene) | — | 76.6 | 76.1 | 08.9 | 09.1 | 1723 |

TABLE 4

Melting points, analytical and IR data for compounds Nos. 24–30

Compound type:

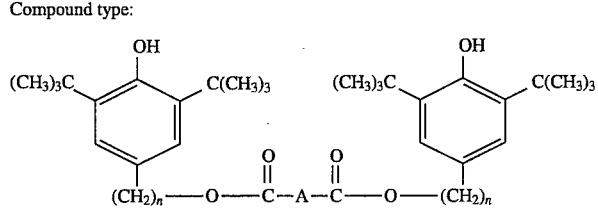

| Compound | | | | ANALYSIS: | | | | IR: 1/λ |
|---|---|---|---|---|---|---|---|---|
| | | | | % C: | | % H: | | |
| No. | n | A | m.p.[°C.] | calc. | found | calc. | found | C=O [cm⁻¹] |
| 24 | 4 | —(CH$_2$)$_4$— | 86–88 | 75.6 | 75.5 | 10.0 | 09.8 | 1734 |
| 25 | 5 | — | 89–90 | 75.2 | 75.1 | 09.8 | 09.9 | 1743 |
| 26 | 5 | —(CH$_2$)$_4$— | 92–95 | 76.0 | 75.6 | 10.2 | 10.0 | 1735 |
| 27 | 6 | — | — | 75.6 | 75.7 | 10.0 | 10.1 | 1743 |
| 28 | 6 | —(CH$_2$)$_2$— | 70 | 76.0 | 75.9 | 10.2 | 10.4 | 1736 |
| 29 | 6 | —(CH$_2$)$_4$— | 54–57 | 76.4 | 76.5 | 10.3 | 10.6 | 1735 |
| 30 | 6 | —(CH$_2$)$_8$— | — | 77.1 | 77.1 | 10.6 | 10.6 | 1735 |

TABLE 5

Analytical and IR data for compounds Nos. 31 to 34

Compound type:

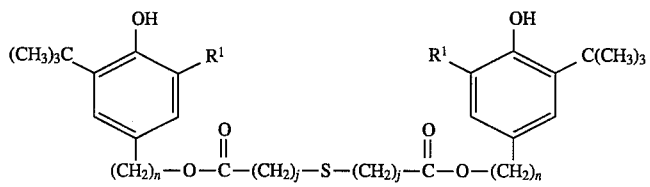

| Compound No. | n | R¹ | j | % C: calc. | % C: found | % H: calc. | % H: found | % S: calc. | % S: found | IR: 1/λ C=O [cm⁻¹] |
|---|---|---|---|---|---|---|---|---|---|---|
| 31 | 4 | CH₃ | 2 | 70.3 | 70.5 | 8.9 | 9.0 | 5.2 | 5.4 | 1731 |
| 32 | 6 | CH₃ | 2 | 71.6 | 71.5 | 9.3 | 9.5 | 4.8 | 4.9 | 1732 |
| 33 | 5 | C(CH₃)₃ | 2 | 72.7 | 72.6 | 9.7 | 9.7 | 4.4 | 4.7 | 1736 |
| 34 | 5 | C(CH₃)₃ | 1 | 72.1 | 72.0 | 9.5 | 9.6 | 4.6 | 4.7 | 1734 |

EXAMPLE 35

Example 23 is repeated except that in place of the product from Example 1b 6-(3,5-di-tert-butyl-4-hydroxyphenyl)hexanol is used as the starting material. The product (compound No. 35) of the formula

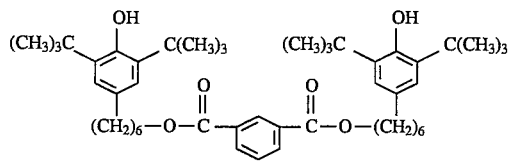

has an IR absorption of the carbonyl band at 1723 cm⁻¹.

Analysis: calculated 77.6% C 9.5% H, found 77.1% C 9.5% H.

EXAMPLE 36

7.57 g (30 mmol) of methyl trimellitate, 33 g (117 mmol) of the product from Example 1b and 0.45 (1.8 mmol) of dibutyltin oxide are mixed in a round-bottomed flask fitted with a fractionating column. The mixture is heated to 180° C., methanol being distilled off. After 2 hours the pressure above the mixture is reduced to 533 hPa (=400 mmHg) and the temperature is then kept at 180° C. for a further 4 hours. The excess 6-(3-tert-butyl-5-methyl-4-hydroxyphenyl)hexanol is then removed by distillation (150° C., 4 Pa) and the resulting crude product is purified by chromatography (SiO₂; first hexane, then hexane/ethyl acetate=19/1). 24.7 g (87%) of a product of the formula

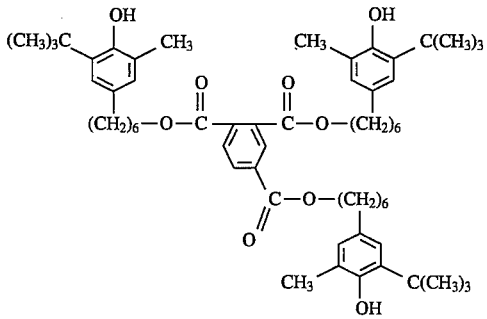

(compound No. 36) are obtained; IR absorption of the carbonyl band at 1722 cm⁻¹.

Analysis: calculated 75.9% C 8.9% H, found 75.3% C 9.3% H.

EXAMPLE 37

16.5 g (70 mmol) of 4-(3-tert-butyl-5-methyl-4-hydroxyphenyl)butanol, 18.05 g (91 mmol) of methyl 10-undecenoate and 80 mg (1.4 mmol) of dibutyltin oxide are introduced into a round-bottomed flask fitted with a fractionating column.

The mixture is heated to 180° C., methanol being distilled off. After 2 hours, the pressure above the mixture is reduced to 400 mmHg and the temperature is then kept at 180° C. for a further 2 hours. The excess methyl 10-undecenoate is then removed by distillation and the resulting crude product (brown oil) is purified by chromatography (SiO₂; hexane/ethyl acetate 9: 1).

23.15 g (82%) of a product of the formula

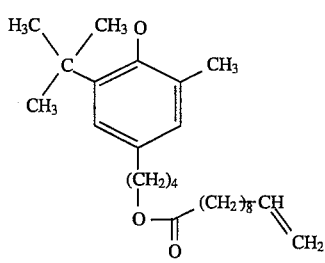

are obtained.

Analytical and IR data: see Table 6.

EXAMPLES 38–42

Compounds 38–42 are prepared analogously to the method described in Example 1. Analytical and IR data of compounds 38–40 are given in Table 6 and the corresponding data for compounds 40 and 41 are given in Table 7.

TABLE 6

Analytical and IR data for compounds Nos. 37–40; compound type:

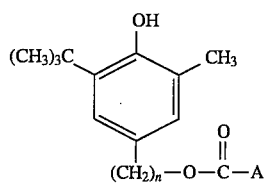

| Compound | | | ANALYSIS: | | | | IR: 1/λ |
|---|---|---|---|---|---|---|---|
| | | | % C: | | % H: | | |
| No. | n | A | calc. | found | calc. | found | C=O [$cm^{-1}$] |
| 37 | 4 | $-(CH_2)_8-CH=CH_2$ | 77.56 | 77.59 | 10.52 | 10.58 | 1719/1735 |
| 38 | 4 | $-C(CH_3)=CH_2$ | 74.96 | 74.95 | 9.27 | 9.48 | 1705 |
| 39 | 6 | $-CH=CH_2$ | 75.43 | 75.20 | 9.50 | 9.53 | 1712/1725 |
| 40 | 6 | $-C(CH_3)=CH_2$ | 75.86 | 75.83 | 9.70 | 10.16 | 1705/1718 |

TABLE 7

Analytical and IR data for compounds Nos. 41 and 42

Compound type:

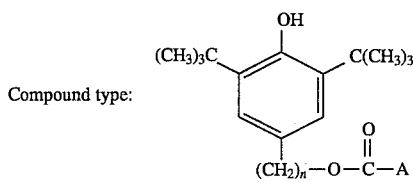

| Compound | | | ANALYSIS: | | | | IR: 1/λ |
|---|---|---|---|---|---|---|---|
| | | | % C: | | % H: | | |
| No. | n | A | calc. | found | calc. | found | C=O [$cm^{-1}$] |
| 41 | 6 | $-CH=CH_2$ | 76.61 | 76.44 | 10.06 | 10.08 | 1725 |
| 42 | 6 | $-C(CH_3)=CH_2$ | 76.96 | 76.85 | 10.23 | 10.16 | 1719 |

EXAMPLES 43–45

Compound No. 43 is prepared by the method described in Example 1; compound No. 44 is prepared by the method described in Example 37; compound No. 45 is prepared by the method described in Example 23. Analytical and IR data for compounds 43–45 are given in Table 8.

TABLE 8

Analysis and IR data for compounds Nos. 43–45

Compound type:

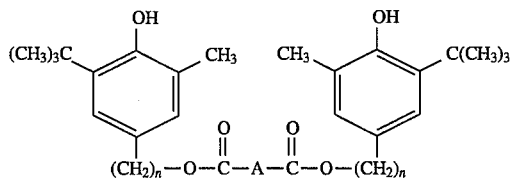

| Compound No. | n | A | ANALYSIS: % C: calc. | found | % H: calc. | found | IR: 1/λ C=O [cm⁻¹] |
|---|---|---|---|---|---|---|---|
| 43 | 4 | —CH₂—CH₂— | 73.61 | 73.14 | 9.08 | 9.21 | 1722 |
| 44 | 4 | —(CH₂)₂—O—(CH₂)₂— | 72.21 | 71.93 | 9.09 | 9.20 | 1728 |
| 45 | 6 | (thiophene-2,5-diyl) | 72.25 | 72.41 | 8.49 | 8.53 | 1717 |

% S: calc. 4.82    found 4.69

EXAMPLE 46 a) Esterification of the dicarboxylic acid mixture with methanol 22 ml/0.41 mol of concentrated sulfuric acid are added dropwise at 10° C. to a solution of 52 g (0.4 mol) of dicarboxylic acid mixture (manufacturer BASF; comprising 25–35% of succinic acid, 37–47% of glutaric acid and 25–30% of adipic acid) in 450 ml of methanol. The resulting solution is kept at the reflux temperature for 3 hours. After cooling to 20°–25° C., the mixture is neutralised with 55 g of potassium carbonate, poured into water and extracted with ethyl acetate. Evaporation of the solvent yields 23 g (36%) of the desired ester mixture in the form of a pale yellow oil.

Gas chromatographic analysis of the compound mixture of the formula $H_3C—OCO—(CH_2)_x—COO—CH_3$:

x=2  23 mol-%
x=3  44 mol-%
x=4  33 mol-% b) Preparation of compound 46

30.7 g (130 mmol) of 4-(3-tert-butyl-5-methyl-4-hydroxyphenyl)butanol, 8.01 g (50 mmol) of the diester mixture described under (a) and 490 mg (2 mmol) of dibutyltin oxide are introduced into a round-bottomed flask provided with a fractionating column.

The mixture is heated to 180° C., methanol being distilled off. The mixture is kept at 180° C. for a further 15 hours. After cooling to 20°–25° C., the crude mixture is purified by chromatography (SiO₂; hexane/ethyl acetate 40:1→19:1→9:1).

17.1 g (60%) of compound No. 46 are obtained in the form of a yellow oil.

Analytical and IR data: see Table 9.

EXAMPLES 47–51

The preparation of compounds 47–48 is carried out using corresponding phenolic alcohols in accordance with the method described in Example 46.

In order to prepare compounds 49, 50 and 51, the corresponding methyl ester is first synthesised from Poly-THF-Dipropionic acid® 350 (manufacturer: Bayer A.G., Leverkusen) by the method described in Example 46. The high molecular weight dicarboxylic acid methyl ester thus obtained is then reacted using corresponding phenolic alcohols in accordance with the method described in Example 46 to give the said end products.

Analytical and IR data for compounds 46-51 are given in Table 9.

TABLE 9

Analytical and IR data for compounds 46–51
Compound type (diester mixtures and oligomers)

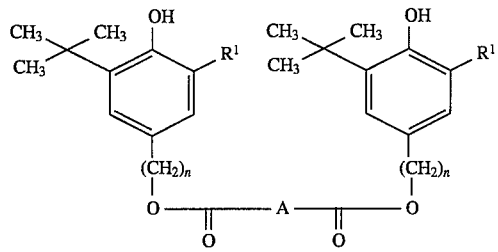

| Compound | | | | ANALYSIS: | | | | IR: 1/λ |
|---|---|---|---|---|---|---|---|---|
| | | | | C %: | | H %: | | |
| No. | $R^1$ | n | A | calc. | found | calc. | found | C=O [cm$^{-1}$] |
| 46 | Me | 4 | $-(CH_2)_x-$ where x = 2 20–25%; x = 3 40–43%; x = 4 34–38% | 73.91* | 73.79 | 9.22 | 9.37 | 1719 |
| 47 | t-Bu | 4 | | 75.43* | 75.05 | 9.88* | 9.98 | 1735 |
| 48 | Me | 6 | 21% x = 2; 42% x = 3; 37% x = 4; m.p. 79–93° C. | 74.96* | 74.91 | 9.68* | 9.81 | 1720 |
| 49 | Me | 4 | $-(CH_2)_2-O+(CH_2)_4-O\}_y-(CH_2)_2-$ y ≅ 2.6 | 70.26 | 69.92 | 9.61 | 9.78 | 1735 |
| 50 | t-Bu | 4 | | 71.61 | 71.92 | 9.95 | 10.21 | 1737 |
| 51 | Me | 6 | | 71.70 | 71.18 | 9.96 | 9.97 | 1736 |

Me = methyl; t-Bu = tert-butyl
*Analysis calculated for x = 3

EXAMPLE 52 a) Preparation of methyl nitrilotriacetate 74.8 ml (137.7 g; 1.4 mol) of concentrated sulfuric acid are added dropwise to a suspension of 100 g (0.52 mol) of nitrilotriacetic acid in 200 ml of methanol at about 10° C.

The mixture is kept at the reflux temperature for 22 hours. After cooling to room temperature, the mixture is neutralised by careful addition of 150 g of potassium carbonate, poured into water and extracted with ethyl acetate.

Evaporation of the solvent and drying of the residue under vacuum yields 57 g (47%) of methyl nitrilotriacetate in the form of a colourless oil.

IR (film on KBr crystal): carbonyl absorption at 1751 cm$^4$

Analysis: calc. 46.35% C, 6.48% H, 6.0% N found 46.47% C, 6.53% H, 6.14% N b) Preparation of compound 52 1.76 g (7.5 mmol) of methyl nitrilotriacetate, 7 g (29.4 mmol) of 4-(3-tert-butyl-5-methyl-4-hydroxyphenyl)butanol and 25 mg (0.45 mmol) of dibutyltin oxide are introduced into a round-bottomed flask provided with a fractionating column. The mixture is heated to 180° C., methanol being distilled off. After 3 hours, the pressure is reduced to 400 mmHg and the mixture is kept at 180° C. for a further 2 hours.

The excess 4-(3-tert-butyl-5-methyl-4-hydroxyphenyl)butanol is then removed by distillation (150° C./0.4 Pa) and the resulting crude product is purified by chromatography (SiO$_2$; hexane-ethyl acetate 9:1→3: 1).

5.6 g (88%) of a product of the formula

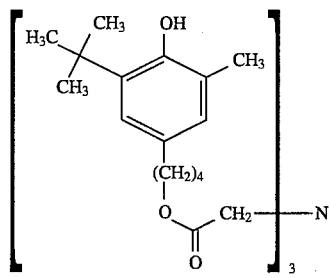

are obtained.

Analytical and IR data: see Table 10.

EXAMPLES 53–55

Compounds 53–55 are prepared by the method described in Example 52. Analytical and IR data of the compounds are summarised in Table 10.

TABLE 10

Compound type:

$$\left[ \begin{array}{c} \text{(3,5-di-substituted-4-hydroxyphenyl)-(CH}_2)_n\text{-O-C(=O)-CH}_2\text{-N} \end{array} \right]_3$$

with 2-(1,1-dimethylethyl) / CH₃ groups and R¹ on the phenol ring

| Compound No. | R¹ | n | m.p. | C %: calc. | C %: found | H %: calc. | H %: found | N %: calc. | N %: found | IR: 1/λ C=O [cm⁻¹] |
|---|---|---|---|---|---|---|---|---|---|---|
| 52 | Me | 4 | — | 72.39 | 72.39 | 8.93 | 8.83 | 1.66 | 1.48 | 1738 |
| 53 | t-Bu | 4 | — | 74.11 | 73.42 | 9.64 | 9.68 | 1.44 | 1.23 | 1747 |
| 54 | Me | 6 | — | 73.59 | 72.98 | 9.43 | 9.67 | 1.51 | 1.31 | 1739 |
| 55 | t-Bu | 6 | — | 75.03 | 74.18 | 10.02 | 10.28 | 1.33 | 1.33 | 1748 |

EXAMPLES 56–60

Compounds 56–60 are prepared by the method described in Example 36. Analytical and IR data of the compounds are summarised in Table 11.

TABLE 11

Compound type: [(3-(1,1-dimethylethyl)-5-R¹-4-hydroxyphenyl)-(CH₂)₆-O-C(=O)-]_z A

| Compound No. | R¹ | A | z | m.p. °C. | C %: calc. | C %: found | H %: calc. | H %: found | IR: 1/λ C=O [cm⁻¹] |
|---|---|---|---|---|---|---|---|---|---|
| 56 | t-Bu | 1,2,4-benzene | 3 | — | 77.05 | 77.28 | 9.56 | 9.53 | 1727 |
| 57 | Me | 1,3,5-benzene | 3 | 62–65 | 75.91 | 75.95 | 8.92 | 8.92 | 1728 |
| 58 | t-Bu | 1,3,5-benzene | 3 | 95–97 | 77.05 | 76.09 | 9.56 | 9.67 | 1729 |
| 59 | Me | 1,2,4,5-benzene | 4 | — | 75.57 | 74.95 | 8.94 | 9.65 | 1725 |

TABLE 11-continued

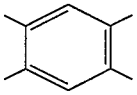

| Compound No. | R¹ | A | z | m.p. °C. | ANALYSIS: C %: calc. | found | H %: calc. | found | IR: 1/λ C=O [cm⁻¹] |
|---|---|---|---|---|---|---|---|---|---|
| 60 | t-Bu | | 4 | — | 76.77 | 71.14 | 9.59 | 8.91 | 1730 |

EXAMPLE 61

Preparation of 4-(3,5-dicyclohexyl-4-hydroxyphenyl-)hexanol 258 g (1 mol) of 2,6-dicyclohexylphenol and 591 g (5 mol) of 1,6-hexanediol are melted in a sulfonation flask and heated with 36 g (0.64 mol) of potassium hydroxide for 10 hours at 238° C. The mixture is then slightly acidified at 80° C. using a 2 molar aqueous HCl solution. The phases are separated, the inorganic phase is washed with toluene and the combined organic phases are concentrated in a rotary evaporator. Excess 1,6-hexanediol and unreacted 2,6-dicyclohexylphenol are removed by distillation.

Crystallisation of the residue from special boiling point benzine (80°–110° C.) yields 163 g (45%) of a product of the formula

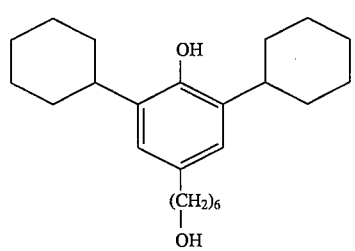

m.p.: 96° C.

Analysis: calc. 80.39% C, 10.68% H found 78.62% C, 10.62% H

EXAMPLE 62

32.3 g (90 mmol) of 4-(3,5-dicyclohexyl-4-hydroxyphenyl)hexanol are reacted using 9.2 g (50 mmol) of adipic acid dichloride, in accordance with the method described in Example 1c, to give 18.7 g (47%) of a product of the formula

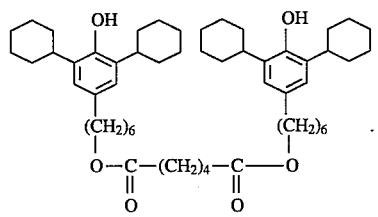

The compound is obtained in the form of a viscous oil.

IR (film on KBr crystal): 1736, 1717 cm⁻¹ (C=O)

Analysis: calc. 77.76% C, 10.29% H found 77.62% C, 10.05% H

Use examples

EXAMPLE 63

Stabilisation of polypropylene 100 parts of polypropylene powder, containing 0.1% of calcium stearate, are mixed with 0.3% of distearyl thiodipropionate (DSTDP) and 0.1% of the stabiliser according to the invention indicated in Table 12 and the mixture is then kneaded for 10 minutes at 200° C. in a Brabender plastograph.

The composition thus obtained is pressed in a press which has a surface temperature of 260° C. to give 1 mm thick plates, from which strips 1 cm wide and 10 cm long are punched. For comparison purposes, a further sample is prepared without stabilisers. Several such strips from each plate are suspended in a circulating air oven heated to 135° C. or 149° C. and observed at regular intervals. The oxidative decomposition of these strips can be recognised by an incipient circular yellow discoloration. The time in days until decomposition takes place is a criterion for the stability of the sample.

TABLE 12

Time (in days) before decomposition of the samples containing the stabiliser combination 0.3% DSTDP + 0.1% compound according to the invention and containing no stabiliser takes place

| Stabilisers | Number of days oven ageing before decomposition takes place | |
|---|---|---|
| | at 135° C. | at 149° C. |
| none | 1 | <1 |
| DSTDP + compound No. 8 | 126 | 50 |
| DSTDP + compound No. 13 | 115 | 40 |
| DSTDP + compound No. 17 | 156 | 65 |
| DSTDP + compound No. 20 | 162 | 60 |
| DSTDP + compound No. 21 | 175 | 38 |
| DSTDP + compound No. 22 | 247 | 57 |
| DSTDP + compound No. 23 | 245 | 85 |
| DSTDP + compound No. 24 | 140 | 43 |
| DSTDP + compound No. 25 | 121 | 24 |
| DSTDP + compound No. 26 | 151 | 33 |
| DSTDP + compound No. 28 | 147 | 47 |
| DSTDP + compound No. 29 | 145 | 49 |
| DSTDP + compound No. 30 | 194 | 50 |
| DSTDP + compound No. 35 | 148 | 50 |
| DSTDP + compound No. 36 | 190 | 71 |
| DSTDP + compound No. 52 | 158 | 55 |
| DSTDP + compound No. 53 | 158 | 48 |
| DSTDP + compound No. 54 | 161 | 55 |
| DSTDP + compound No. 55 | 150 | 43 |
| DSTDP + compound No. 56 | 170 | 52 |
| DSTDP + compound No. 57 | 193 | 70 |
| DSTDP + compound No. 58 | 173 | 52 |
| DSTDP + compound No. 59 | 163 | 63 |
| DSTDP + compound No. 60 | 159 | 48 |

TABLE 13

Yellowness Index after 45 minute oven ageing of samples containing no stabilisers, 0.5% of dilauryl thiodipropionate (DLTDP) and also 0.5% DLTDP + 0.25% of the indicated compound according to the invention

| Stabilisers | Yellowness Index after 45 minutes at 180° C. |
|---|---|
| none | 78 |
| DLTDP | 75 |
| DLTDP + compound No. 1 | 26 |
| DLTDP + compound No. 7 | 25 |
| DLTDP + compound No. 8 | 26 |
| DLTDP + compound No. 12 | 34 |
| DLTDP + compound No. 13 | 39 |
| DLTDP + compound No. 15 | 33 |
| DLTDP + compound No. 16 | 34 |
| DLTDP + compound No. 17 | 26 |
| DLTDP + compound No. 19 | 31 |
| DLTDP + compound No. 20 | 26 |
| DLTDP + compound No. 21 | 33 |
| DLTDP + compound No. 22 | 21 |
| DLTDP + compound No. 23 | 29 |
| DLTDP + compound No. 24 | 32 |
| DLTDP + compound No. 25 | 41 |
| DLTDP + compound No. 26 | 28 |
| DLTDP + compound No. 28 | 30 |
| DLTDP + compound No. 29 | 32 |
| DLTDP + compound No. 31 | 29 |
| DLTDP + compound No. 32 | 27 |
| DLTDP + compound No. 33 | 32 |
| DLTDP + compound No. 34 | 30 |
| DLTDP + compound No. 39 | 36 |
| DLTDP + compound No. 40 | 26 |
| DLTDP + compound No. 42 | 32 |

EXAMPLE 63

Stabilisation of acrylonitrile-butadiene-styrene terpolymer (ABS)

The stabilisers indicated in Table 13 are dissolved in 40 ml of a mixture of hexane and isopropanol. The solution is added to a dispersion of 100 g of ABS in 600 ml of water, with vigorous stirring, after which the solution is completely absorbed by the ABS within about one minute. The polymer powder containing the stabilisers is then filtered off and dried for 40 hours at 40° C. under vacuum.

For comparison purposes, the subsequent processing steps are also carried out using a sample without stabilisers.

2% of titanium dioxide, as pigment, and 1% of ethylene-bis-stearic acid amide, as lubricant, are added to the dry powder. The mixture is then compounded within 4 minutes on a 2-roll mill at 180° C.

A plate 0.8 mm thick is pressed from the rolled sheet at 175° C. and 45×17 mm² test pieces are punched from this plate. The test to determine the effectiveness of the added stabilisers is carried out by heat ageing in a circulating air oven at 180° C. The criterion is the colour development after a test time of 45 minutes. The colour intensity is determined in accordance with ASTM D 1925-70 (yellowness Index). The test results are summarised in Table 13. Higher figures indicate more intensive yellowing. The tests show that yellowing is effectively suppressed by the compounds according to the invention.

EXAMPLE 64

Stabilisation of X-SBR latex (carboxylated SBR latex)

In each case 0.25 parts by weight of the compounds according to the invention listed in Table 14 are dissolved in a little methanol and stirred into 100 parts by weight of X-SBR latex (styrene-butadiene copolymer). A precisely defined amount of latex is then filled into Petri dishes and dried in an oven at 80° C. Transparent films having a layer thickness of about 0.2 mm are obtained. For comparison purposes, a sample without stabilisers is prepared.

The test to determine the effectiveness of the added stabilisers is carried out by heat ageing in a circulating air oven at 135° C. The discoloration of the samples is determined in accordance with ASTM D 1925-70 (yellowness Index) after the intervals indicated in Table 14. The test results are summarised in Table 14. Higher figures indicate more intensive yellowing. The tests show that yellowing is effectively suppressed by the compounds according to the invention.

TABLE 14

Yellowness Index after the indicated ageing time at 135° C.

| Stabiliser | Yellowness Index after ageing time (in hours) | | | |
|---|---|---|---|---|
| | 4 h | 12 h | 24 h | 40 h |
| none | 92 | * | * | * |
| 0.25% compound No. 31 | 46 | 52 | 64 | 75 |
| 0.25% compound No. 32 | 40 | 46 | 58 | 69 |

*: not measurable (sample black)

What is claimed is:

1. A compound of the formula I

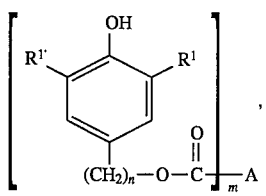

(I)

in which n is an integer from the range from 4 to 8 and m is an integer from the range from 1 to 4;

if m=1, A is $C_1$–$C_{25}$alkyl, which is unsubstituted or substituted by $C_5$–$C_8$cycloalkyl; or is $C_2$–$C_{25}$alkyl which is interrupted by $C_5$–$C_8$cycloalkyl or one or more groups selected from —S—, —O— and —NR$^2$—; or, if m=1, A is $C_5$–$C_8$cycloalkyl, which is unsubstituted or substituted by $C_1$–$C_{12}$alkyl or $C_2$–$C_{12}$alkenyl; $C_6$–$C_8$cycloalkenyl, which is unsubstituted or substituted by $C_1$–$C_{12}$alkyl or $C_2$–$C_{12}$alkenyl; phenyl, which is unsubstituted or substituted by $C_1$–$C_{12}$alkyl or $C_2$–$C_{12}$alkenyl; naphthyl, which is unsubstituted or substituted by $C_1$–$C_{12}$alkyl or $C_2$–$C_{12}$alkenyl; biphenyl, which is unsubstituted or substituted by $C_1$–$C_{12}$alkyl or $C_2$–$C_{12}$alkenyl; $C_2$–$C_{25}$alkenyl; $C_6$–$C_{10}$bicycloalkenyl; $C_7$–$C_{12}$phenylalkyl; $C_8$–$C_{12}$phenylalkenyl; $C_{11}$–$C_{16}$naphthylalkyl; $C_{12}$–$C_{16}$naphthylalkenyl; $C_{13}$–$C_{18}$biphenylalkyl; $C_{14}$–$C_{18}$biphenylalkenyl; a group of the formula II

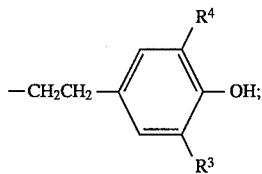

(II)

if m=2, A is a direct bond; $C_1$–$C_{12}$alkylene; $C_2$–$C_{12}$alkenylene; $C_5$–$C_8$cycloalkylene, which is unsubstituted or substituted by $C_1$–$C_{12}$alkyl or $C_2$–$C_{12}$alkenyl; $C_6$–$C_8$cycloalkenylene, which is unsubstituted or substituted by $C_1$–$C_{12}$alkyl or $C_2$–$C_{12}$alkenyl; $C_6$–$C_{10}$bicycloalkenylene; phenylene; naphthylene; a divalent heterocyclic radical from the group comprising furan, thiophene or pyrrole, which is saturated on the nitrogen atom by hydrogen or the substituent —R$^2$; or, if m=2, A is $C_2$–$C_{36}$alkylene which is interrupted by $C_5$–$C_8$cycloalkylene or phenylene or one or more groups selected from —O— and —NR$^2$—;

if m=3, A is $C_1$–$C_8$alkanetriyl; $C_2$–$C_8$alkenetriyl; benzenetriyl; naphthalenetriyl; or $C_2$–$C_{18}$alkanetriyl, which is interrupted by at least one of the groups —S—, —O— or —NR$^2$—;

if m=4, A is a benzene radical, naphthyl radical, tetrahydrofuryl radical or cyclohexyl radical having 4 free valencies;

R$^1$ and R$^{1'}$, independently of one another, are $C_1$–$C_{10}$alkyl or $C_5$–$C_8$cycloalkyl;

R$^2$ is H or $C_1$–$C_4$alkyl;

R$^3$ and R$^4$, independently of one another, are $C_1$–$C_4$alkyl; and with the proviso that, when n is 4, R$^{1'}$ tert-butyl or cyclohexyl, and R$^1$ is methyl, tert-butyl or cyclohexyl, and with the further proviso that, when A contains an ethylenic double bond, R$^{1'}$ is tert-butyl and R$^1$ is methyl.

2. A compound of the formula I according to claim 1, in which R$^{1'}$ has the meaning of secondary or tertiary $C_3$–$C_{24}$alkyl or $C_5$–$C_8$cycloalkyl; and R$^1$ has the meaning $C_1$–$C_{10}$alkyl or $C_8$–$C_8$cycloalkyl.

3. A compound of the formula I according to claim 1, in which R$^{1'}$ has the meaning tert-butyl and R$^1$ has the meaning methyl.

4. A compound of the formula I according to claim 1, in which if m=1, A is $C_1$–$C_{25}$alkyl, which is unsubstituted or substituted by $C_5$–$C_8$cycloalkyl; or $C_2$–$C_{25}$alkyl, which is interrupted by $C_5$–$C_8$cycloalkyl or one or more groups selected from —S—, —O— and —NR$^2$—; or if m=1, A is $C_5$–$C_8$cycloalkyl, which is unsubstituted or substituted by $C_1$–$C_{12}$alkyl; $C_6$–$C_8$cycloalkenyl, which is unsubstituted or substituted by $C_1$–$C_{12}$alkyl; phenyl, which is unsubstituted or substituted by $C_1$–$C_{12}$alkyl; or $C_2$–$C_{25}$alkenyl; $C_7$–$C_{12}$phenylalkyl; or a group of the formula II

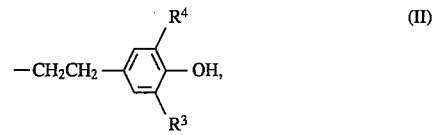

(II)

if m=2, A is a direct bond; $C_1$–$C_{12}$alkylene; $C_2$–$C_{12}$alkenylene; $C_5$–$C_8$cycloalkylene, which is unsubstituted or substituted by $C_1$–$C_{12}$alkyl; $C_6$–$C_8$cycloalkenylene, which is unsubstituted or substituted by $C_1$–$C_{12}$alkyl; phenylene; a divalent heterocyclic radical from the group comprising furan, thiophene or pyrrole, which is saturated on the nitrogen atom by hydrogen or the substituent —R$^2$; or, if m=2, A is $C_2$–$C_{18}$alkylene which is interrupted by $C_5$–$C_8$cycloalkylene or phenylene or one or more groups selected from —O— and —NR$^2$—; and if m=3, A is $C_1$–$C_8$alkanetriyl; $C_2$–$C_8$alkenetriyl; benzenetriyl; or $C_2$–$C_{18}$alkanetriyl, which is interrupted by one or more groups selected from —S—, —O— and —NR$^2$—; and if m=4, A is a benzene or cyclohexyl radical having 4 free valencies.

5. A compound of the formula I according to claim 1, in which R$^{1'}$ is tert-butyl or cyclohexyl and R$^1$ is methyl, tert-butyl or cyclohexyl;

n is a number from the range 4 to 6; and if m=1, A is $C_6$–$C_{18}$alkyl or $C_2$–$C_{12}$alkenyl;

if m=2, A is a direct bond; $C_1$–$C_{12}$alkylene; phenylene;

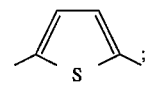

or $C_2$–$C_{36}$alkylene interrupted by 1 to 5; and if m=4, A is a benzene radical having 4 free valencies.

6. A compound of the formula I according to claim 1, in which n is an integer from the range from 5 to 8.

7. A compound of the formula I according to claim 1, in which n is an integer from the range from 6 to 8.

8. A compound of the formula I according to claim 6, in which m is 1 or 2.

9. A compound of the formula I according to claim 8, of the formula

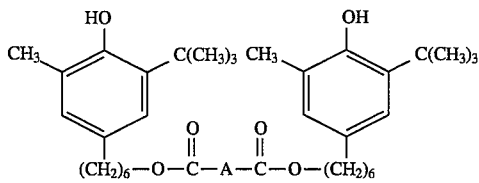

in which A is —(CH$_2$)$_j$—;

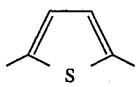

or —(CH$_2$)$_2$—O—[(CH$_2$)$_2$—O—]$_j$—(CH$_2$)$_2$—; j is 0 or an integer from the range from 1 to 4;

10. One of the compounds (a) to (1)
a) 6-(3-tert-butyl-4-hydroxy-5-methylphenyl)hexyl stearate;
b) 6-(3,5-di-tert-butyl-4-hydroxyphenyl)hexyl stearate;
c) bis[6-(3-tert-butyl-4-hydroxy-5-methylphenyl)hexyl]succinate;
d) bis[6-(3-tert-butyl-4-hydroxy-5-methylphenyl)hexyl]adipate;
e) bis[6-(3-tert-butyl-4-hydroxy-5-methylphenyl)hexyl]suberate;
f) bis[6-(3-tert-butyl-4-hydroxy-5-methylphenyl)hexyl]isophthalate;
g) bis[6-(3,5-di-tert-butyl-4-hydroxyphenyl)hexyl]isophthalate;
h) tris[6-(3-tert-butyl-4-hydroxy-5-methylphenyl)hexyl]trimellitate;
j) tris[6-(3,5-di-tert-butyl-4-hydroxyphenyl)hexyl]trimellitate;
k) tris[6-(3-tert-butyl-4-hydroxy-5-methylphenyl)hexyl]trimesate; and
l) tris[6-(3,5-di-tert-butyl-4-hydroxyphenyl)hexyl]trimesate according to claim 1.

11. A composition containing an organic material sensitive to thermal, oxidative and/or actinic degradation and an effective stabilising amount of a compound of the formula I according to claim 1

12. A composition according to claim 11, in which the organic material is a synthetic organic polymer or a mixture of such polymers.

13. A composition according to claim 12, in which the synthetic organic polymer is a polyolefin or a styrene copolymer.

14. A composition according to claim 12, in which the synthetic organic polymer is sensitive to oxidative degradation.

15. A method for stabilising organic material against thermal, oxidative or/and actinic degradation, which method comprises adding an effective stabilising amount of a compound of the formula I according to claim 1 to said material.

16. A compound of the formula Ia

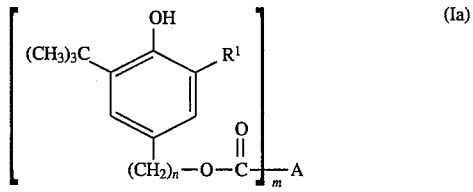

in which n is an integer from the range from 4 to 8 and m is an integer from the range from 1 to 3, if m=1, A is C$_1$–C$_{25}$alkyl, which is unsubstituted or substituted by C$_5$–C$_8$cycloalkyl, or is C$_2$–C$_{25}$alkyl, which is interrupted by C$_5$–C$_8$cycloalkyl or one or more groups selected from —S—, —O— and —NR$^2$—, or, if m=1, A is C$_5$–C$_8$cycloalkyl, which is unsubstituted or substituted by C$_1$–C$_{12}$alkyl or C$_2$–C$_{12}$alkenyl, C$_6$–C$_8$cycloalkenyl, which is unsubstituted or substituted by C$_1$–C$_{12}$alkyl or C$_2$–C$_{12}$alkenyl, phenyl, which is unsubstituted or substituted by C$_1$–C$_{12}$alkyl or C$_2$–C$_{12}$alkenyl, naphthyl, which is unsubstituted or substituted by C$_1$–C$_{12}$alkyl or C$_2$–C$_{12}$alkenyl, biphenyl, which is unsubstituted or substituted by C$_1$–C$_{12}$alkyl or C$_2$–C$_{12}$alkenyl, A is C$_2$–C$_{25}$alkenyl, C$_6$–C$_{10}$bicycloalkenyl, C$_7$–C$_{12}$phenylalkyl, C$_8$–C$_{12}$phenylalkenyl, C$_{11}$–C$_{16}$naphthylalkyl, C$_{12}$–C$_{16}$naphthylalkenyl, C$_{13}$–C$_{18}$biphenylalkyl, C$_{14}$–C$_{18}$biphenylalkenyl, or a group of the formula II

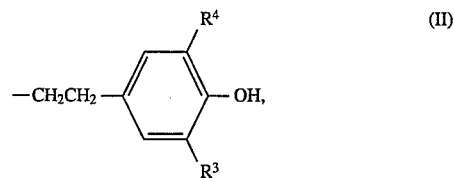

if m=2, A is a direct bond, C$_1$–C$_{12}$alkylene, C$_2$–C$_{12}$alkenylene, C$_5$–C$_8$cycloalkylene, which is unsubstituted or substituted by C$_1$–C$_{12}$alkyl or C$_2$–C$_{12}$alkenyl, A is C$_6$–C$_8$cycloalkenylene, which is unsubstituted or substituted by C$_1$–C$_{12}$alkyl or C$_2$–C$_{12}$alkenyl, A is C$_6$–C$_{10}$bicycloalkenylene, phenylene, naphthylene or C$_2$–C$_{18}$alkylene which is interrupted by C$_5$–C$_8$cycloalkylene or phenylene or one or more groups selected from —O— and —NR$^2$—, if m=3, A is C$_1$–C$_8$alkanetriyl, C$_2$–C$_8$alkenetriyl, benzenetriyl, naphthalenetriyl, or C$_2$–C$_{18}$alkanetriyl which is interrupted by one or more groups selected from —S—, —O— and —NR$^2$—, R$^1$ is methyl or tert-butyl, R$^2$ is H or C$_1$–C$_4$alkyl, R$^3$ and R$^4$, independently of one another, are C$_1$–C$_4$alkyl, and with the proviso that, when n is 4, R$^1$ methyl, tert-butyl or cyclohexyl, and with the further proviso that, when m is 1 or 2 and A is alkenyl or phenylalkenyl or alkenylene, R$^1$ is methyl.

17. A composition containing an organic material sensitive to thermal, oxidative or/and actinic degradation and an effective stabilising amount of a compound of the formula IV

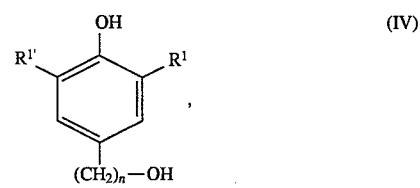

in which n is an integer from the range from 4 to 8 and R$^1$ is method and R$^{1'}$ is tert-butyl 18. A method for stabilising organic material against thermal, oxidative or/and actinic degradation, which method comprises adding an effective stabilising amount of a compound of the formula IV according to claim 17 to said material.

* * * * *